(12) United States Patent
Nishide et al.

(10) Patent No.: US 7,778,381 B2
(45) Date of Patent: Aug. 17, 2010

(54) X-RAY CT APPARATUS

(75) Inventors: Akihiko Nishide, Tokyo (JP); Kosuke Sasaki, Tokyo (JP); Tetsuya Horiuchi, Tokyo (JP)

(73) Assignee: GE Medial Systems Global Technology Company, LLC, Waukesha, WI (US)

( * ) Notice: Subject to any disclaimer, the term of this patent is extended or adjusted under 35 U.S.C. 154(b) by 32 days.

(21) Appl. No.: 12/267,101

(22) Filed: Nov. 7, 2008

(65) Prior Publication Data

US 2009/0122952 A1 May 14, 2009

(30) Foreign Application Priority Data

Nov. 8, 2007 (JP) .............................. 2007-290817

(51) Int. Cl.
*A61B 6/00* (2006.01)

(52) U.S. Cl. .............................. 378/4; 378/111; 378/109

(58) Field of Classification Search ............... 378/4–20, 378/101, 109–112, 114, 115, 901
See application file for complete search history.

(56) References Cited

U.S. PATENT DOCUMENTS

| | | | |
|---|---|---|---|
| 4,417,353 A | 11/1983 | Groh et al. | |
| 4,942,596 A | 7/1990 | Eberhard et al. | |
| 5,432,834 A | 7/1995 | Gershman | |
| 5,478,705 A | 12/1995 | Czekai et al. | |
| 5,661,774 A | 8/1997 | Gordon et al. | |
| 5,762,608 A | 6/1998 | Warne et al. | |
| 5,796,802 A | 8/1998 | Gordon | |
| 5,838,765 A | 11/1998 | Gershman et al. | |
| 2004/0028181 A1 | 2/2004 | Charles, Jr. et al. | |
| 2005/0089133 A1* | 4/2005 | Tsuyuki | 378/8 |
| 2006/0182322 A1 | 8/2006 | Bernhardt et al. | |
| 2008/0056445 A1 | 3/2008 | Spahn | |
| 2008/0144764 A1 | 6/2008 | Nishide et al. | |
| 2008/0212740 A1* | 9/2008 | Sakaguchi et al. | 378/98 |

* cited by examiner

*Primary Examiner*—Courtney Thomas
(74) *Attorney, Agent, or Firm*—Armstrong Teasdale LLP

(57) ABSTRACT

The present invention provides an X-ray CT apparatus capable of obtaining each tomographic image indicative of X-ray tube voltage dependent information of a subject with the optimum image quality by less reduced exposure. The X-ray CT apparatus includes device for setting a plurality of X-ray tube voltages and sets imaging conditions used in the photography using the respective X-ray tube voltages in such a manner that respective image noise of tomographic images photographed at the X-ray tube voltages become substantially identical to one another. The setting of the imaging conditions is the setting of X-ray tube currents. The X-ray tube currents are set based on geometrical characteristic amounts of the subject determined from each scout image in such a manner that the respective image noise of the tomographic images photographed at the plurality of X-ray tube voltages become substantially identical to one another.

20 Claims, 22 Drawing Sheets

FIG. 15A
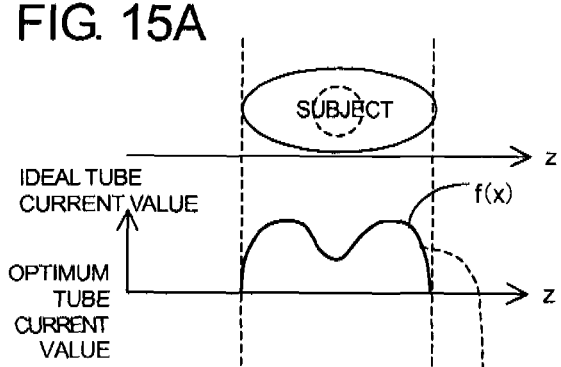
FIG. 15B
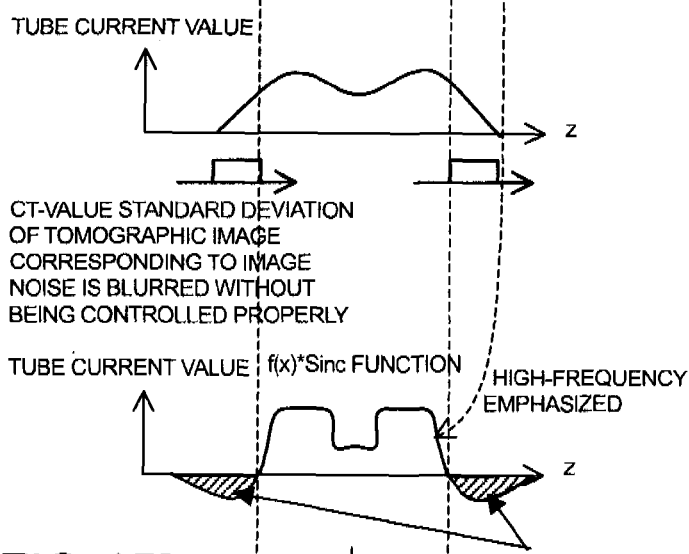
CT-VALUE STANDARD DEVIATION
OF TOMOGRAPHIC IMAGE
CORRESPONDING TO IMAGE
NOISE IS BLURRED WITHOUT
BEING CONTROLLED PROPERLY
FIG. 15C
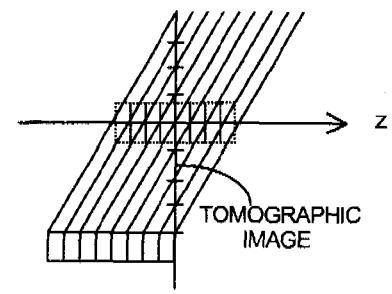
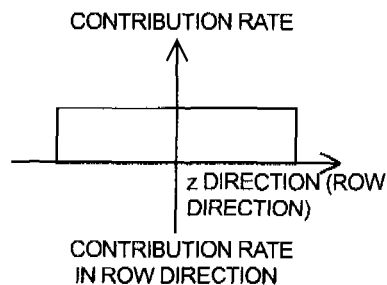
CONTRIBUTION RATE
IN ROW DIRECTION
FIG. 15D
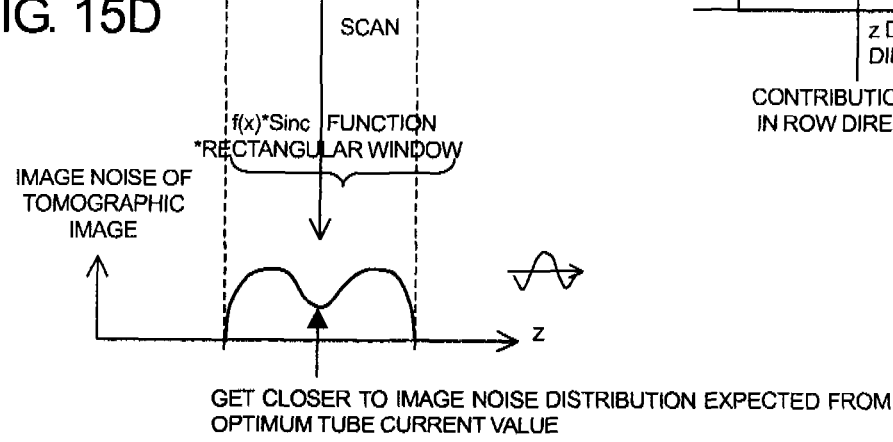
GET CLOSER TO IMAGE NOISE DISTRIBUTION EXPECTED FROM
OPTIMUM TUBE CURRENT VALUE

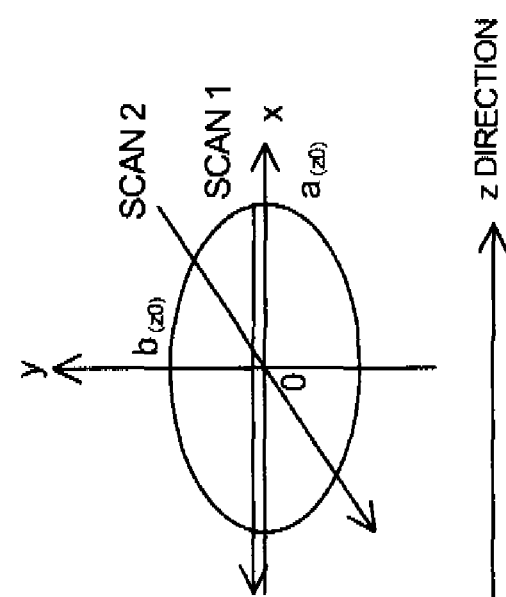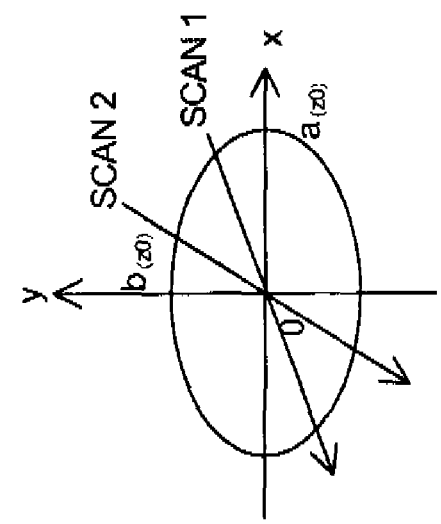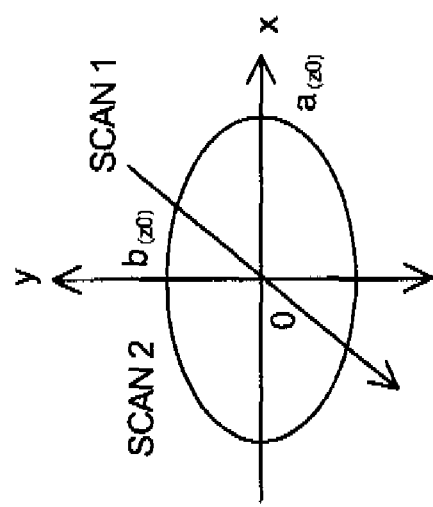

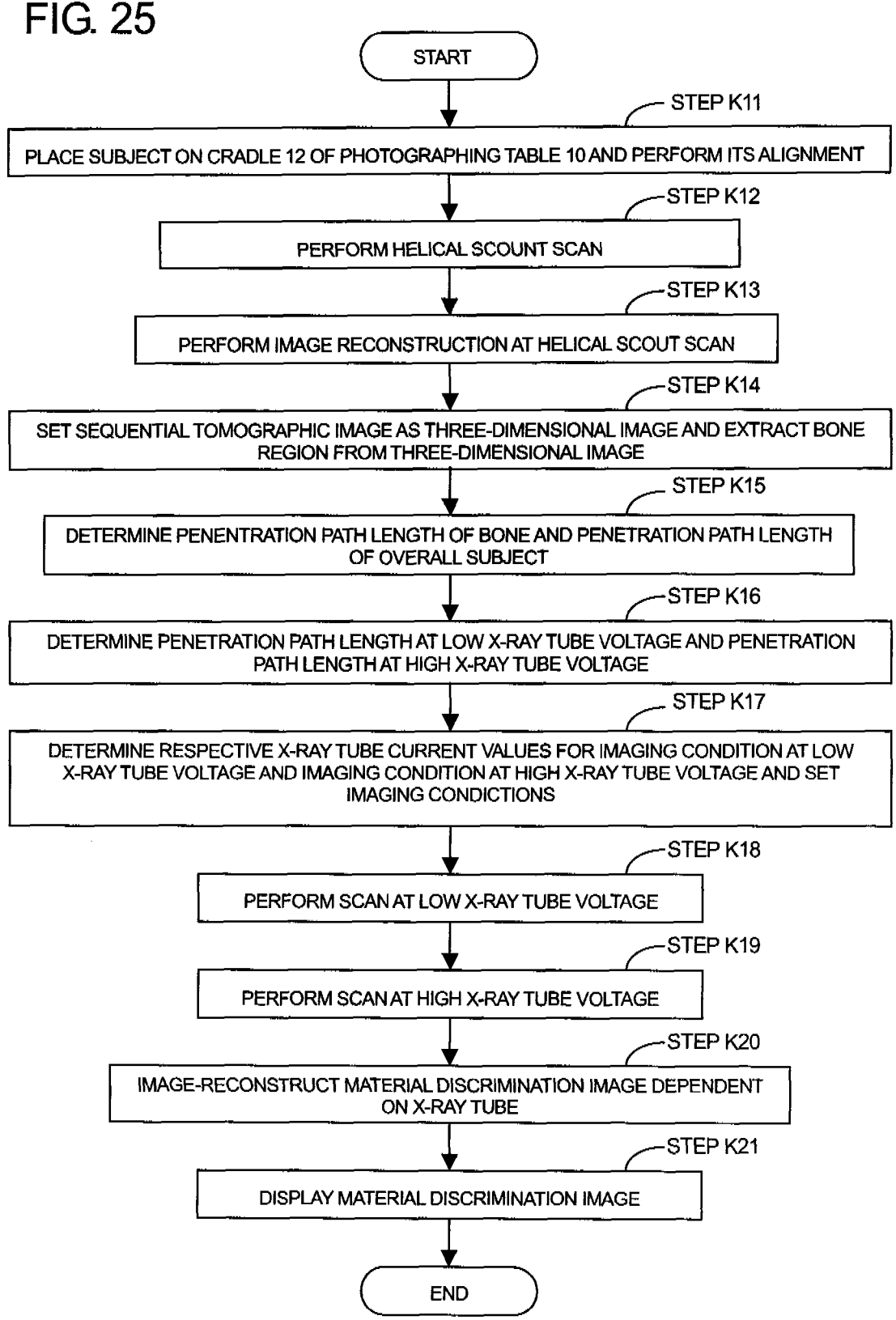

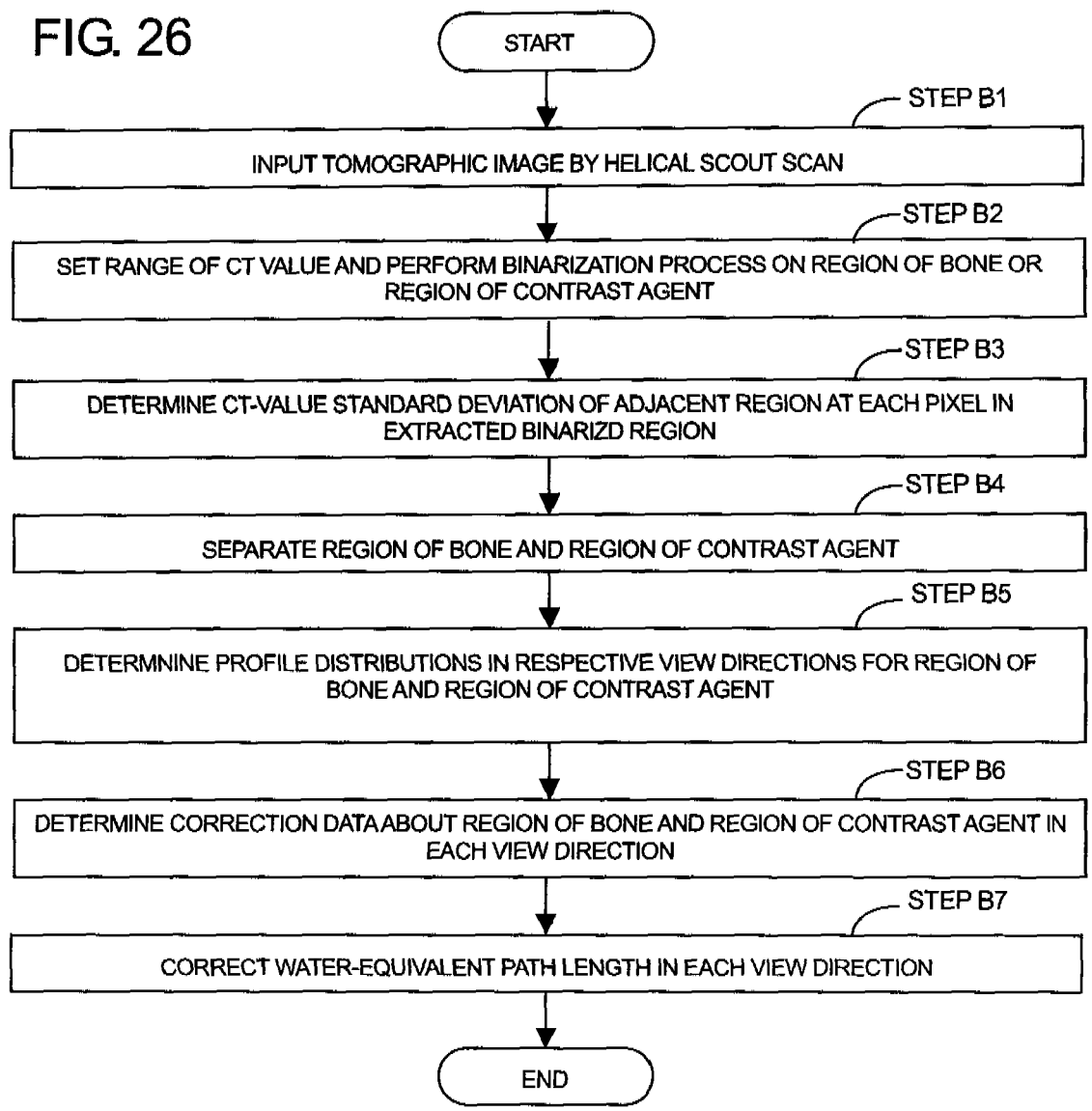

X-RAY CT APPARATUS

CROSS REFERENCE TO RELATED APPLICATIONS

This application claims the benefit of Japanese Patent Application No. 2007-290817 filed Nov. 8, 2007, which is hereby incorporated by reference in its entirety

BACKGROUND OF THE INVENTION

The subject matter disclosed herein relates to a technique of a medical X-ray CT (Computed Tomography) apparatus or an industrial X-ray CT apparatus.

In an X-ray CT apparatus having a multi-row X-ray detector or an X-ray CT apparatus based on a two-dimensional X-ray area detector of a matrix structure typified by a flat panel, there has heretofore been a technique which photographs tomographic images at a plurality of X-ray tube voltages as shown in FIG. 7 and brings information about a difference between the dependencies of X-ray absorption coefficients of materials constituting a subject on the X-ray tube voltages into imaging, based on the tomographic images.

BRIEF DESCRIPTION OF THE INVENTION

However, the process of bringing the information about the difference between the dependencies of the X-ray absorption coefficients on the X-ray tube voltages was a process hard to control the quality of each image obtained by a process for performing weighted subtraction on the tomographic images at the X-ray tube voltages and control noise of the image.

On the other hand, the X-ray CT apparatus having the multi-row X-ray detector or the X-ray CT apparatus based on the two-dimensional X-ray area detector typified by the flat panel has a tendency that as a cone angle of an X-ray cone beam becomes great, the problem of X-ray needless exposure becomes larger. It is therefore necessary to perform photography at a more reduced X-ray dose even upon photographing each tomographic image indicative of the X-ray tube voltage dependent information of each material constituting the subject. It is also necessary to photograph under an imaging condition that can obtain the optimum image quality.

Therefore, an object of the present invention is to provide an X-ray CT apparatus capable of obtaining each tomographic image indicative of X-ray tube voltage dependent information of a subject with the optimum image quality by less reduced exposure.

In a first aspect, there is provided an X-ray CT apparatus comprising X-ray data acquisition means for acquiring X-ray projection data transmitted through a subject lying between an X-ray generator and an X-ray detector detecting X-rays in opposition to the X-ray generator, while the X-ray generator and the X-ray detector are being rotated about the center of rotation lying therebetween, image reconstruction means for image-reconstructing the projection data acquired from the X-ray data acquisition device, image display means for displaying an image-reconstructed tomographic image, and imaging condition setting means for setting various imaging conditions for tomographic image photography, wherein the imaging condition setting means includes means for setting a plurality of X-ray tube voltages and sets imaging conditions used in the photography using the respective X-ray tube voltages in such a manner that respective image noise of tomographic images photographed at the plurality of X-ray tube voltages become substantially identical to one another.

In a second aspect, there is provided the X-ray CT apparatus according to the first aspect, wherein the setting of the imaging conditions is the setting of X-ray tube currents.

In a third aspect, there is provided the X-ray CT apparatus according to the second aspect, wherein the imaging condition setting means determines and sets such X-ray tube currents that respective image noise of tomographic images photographed at a plurality of X-ray tube voltages become substantially identical to one another, based on geometrical characteristic amounts of the subject determined from each scout image.

In a fourth aspect, there is provided the X-ray CT apparatus according to the second or third aspect, wherein the scout image is different in the X-ray tube voltages for photographing the tomographic images, and the X-ray tube currents are determine and set by correcting the subject's geometrical characteristic amounts based on the scout image to amounts equivalents to the X-ray tube voltages for photographing the tomographic images.

In a fifth aspect, there is provided the X-ray CT apparatus according to the fourth aspect, wherein the correction is based on a difference between X-ray penetration path lengths at respective X-ray tube voltages, which have been determined from the scout image.

In a sixth aspect, there is provided the X-ray CT apparatus according to the fifth aspect, wherein the correction is based on a difference between respective X-ray tube voltages, which has been determined using penetration path lengths set for every X-ray tube voltage in a partial region comprised of a predetermined material from a tomographic image of a helical scout scan.

In a seventh aspect, there is provided the X-ray CT apparatus according to the sixth aspect, wherein the partial region comprised of the predetermined material, of the tomographic image of the helical scout scan is of a region defined by a range of a predetermined CT value.

In an eighth aspect, there is provided the X-ray CT apparatus according to any one of the third through seventh aspects, wherein the imaging condition setting means includes determining and setting an optimum X-ray tube current satisfying an index of desired image quality, based on the scout image.

In a ninth aspect, there is provided the X-ray CT apparatus according to any one of the first through eighth aspects, wherein the image reconstruction means extracts X-ray tube voltage dependent information using the X-ray projection data obtained by the photography of the plurality of X-ray tube voltages and brings the same into imaging.

In a tenth aspect, there is provided the X-ray CT apparatus according to the ninth aspect, wherein the process of extracting the X-ray tube voltage dependent information by the photography of the plurality of X-ray tube voltages and bringing the same into imaging is performed in an image space.

In an eleventh aspect, there is provided the X-ray CT apparatus according to the ninth aspect, wherein the process of extracting the X-ray tube voltage dependent information by the photography of the X-ray tube voltages and bringing the same into imaging is performed in an X-ray projection data space.

In a twelfth aspect, there is provided the X-ray CT apparatus according to the tenth or eleventh aspect, wherein the process of extracting the X-ray tube voltage dependent information and bringing the same into imaging includes a weighted subtraction process.

In a thirteenth aspect, there is provided the X-ray CT apparatus according to any one of the ninth through twelfth aspects, wherein the X-ray tube voltage dependent information is information dependent on each material within the subject.

According to the X-ray CT apparatus of the present invention, an advantageous effect is brought about in that an X-ray CT apparatus capable of obtaining each tomographic image indicative of X-ray tube voltage dependent information of a subject with the optimum image quality by more reduced exposure can be realized.

BRIEF DESCRIPTION OF THE DRAWINGS

FIGS. 15A through 15D are diagrams illustrating an ideal tube current value table of a two-dimensional X-ray area detector.

FIGS. 18A, 18B, and 18C are diagrams showing a conventional scan (axial scan) or a cine scan.

FIG. 25 is a flow chart for determining imaging conditions for two types of X-ray tube voltages using a scout image by a helical scout scan.

FIG. 26 is a conceptual diagram of a method for determining profile distributions of regions for a bone and a contrast agent.

DETAILED DESCRIPTION OF THE INVENTION

Figure 1:
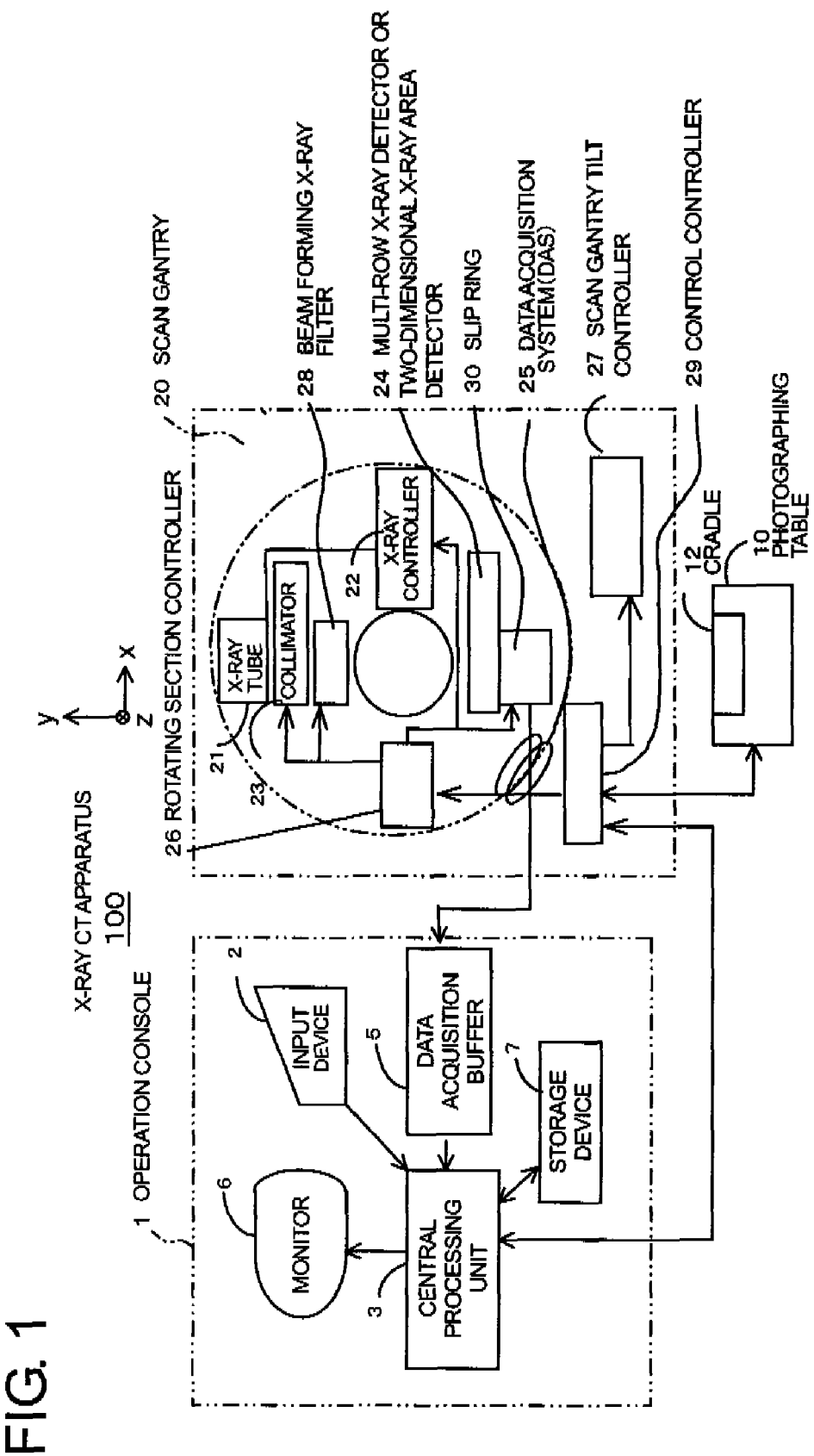
FIG. 1 is a block diagram showing an X-ray CT apparatus according to one embodiment of the present invention.

The present invention will hereinafter be described in further detail by embodiments illustrated in the drawings. Incidentally, the present invention is not limited thereby.

FIG. 1 is a configuration block diagram of an X-ray CT apparatus according to one embodiment of the present invention. The X-ray CT apparatus 100 is equipped with an operation console 1, a photographing table 10 and a scan gantry 20.

The operation console 1 is equipped with an input device 2 which receives an input from an operator, a central processing unit 3 which executes a pre-process, an image reconstructing process, a post-process, etc. a data acquisition buffer 5 which acquires or collects X-ray detector data acquired by the scan gantry 20, a monitor 6 which displays a tomographic image image-reconstructed from projection data obtained by pre-processing the X-ray detector data, and a storage device 7 which stores programs, X-ray detector data, projection data and X-ray tomographic images therein.

Figure 6:
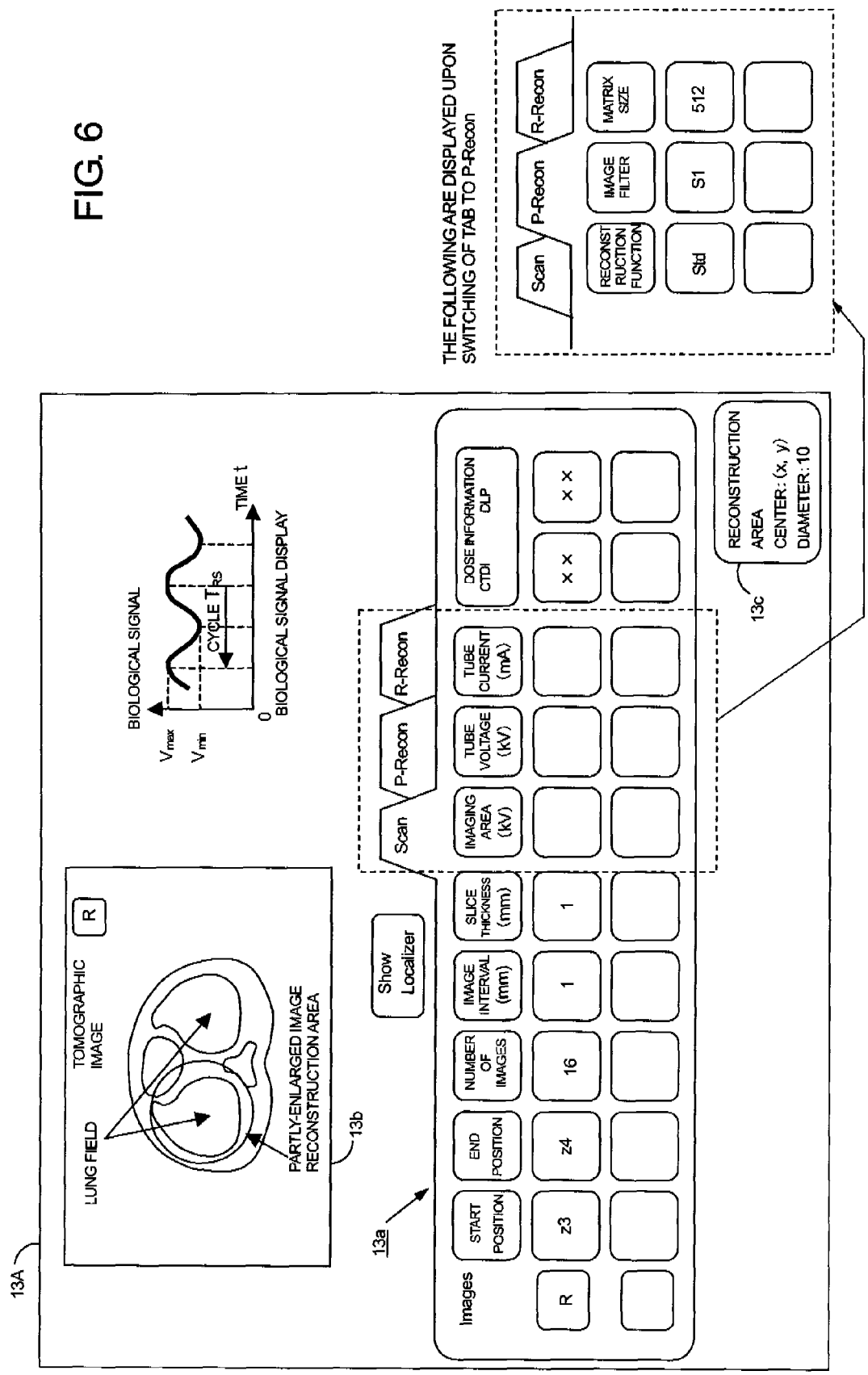
FIG. 6 is a diagram showing an imaging condition input screen of the X-ray CT apparatus.

An input for imaging or photographing conditions is inputted from the input device 2 and stored in the storage device 7. An example of an imaging condition input screen is shown in FIG. 6. An input button 13a for performing a predetermined input is displayed on a scanning or imaging condition input screen 13A. A screen on which a scan tab is being selected is shown in FIG. 6. When P-Recon is selected as the tab, an input display is switched as drawn below FIG. 6. A tomographic image 13b is displayed above the input button 13a, and a reconstruction area 13c is displayed therebelow. If necessary, then biological signals such as a respiratory signal, a heartbeat or cardiac signal, etc. may be displayed as represented in the top right of the screen.

The photographing table 10 includes a cradle 12 that inserts and draws a subject into and from a bore or aperture of the scan gantry 20 with the subject placed thereon. The cradle 12 is elevated and moved linearly on the photographing table 10 by a motor built in the photographing table 10.

The scan gantry 20 includes an X-ray tube 21, an X-ray controller 22, a collimator 23, a beam forming X-ray filter 28, a multi-row X-ray detector 24 and a DAS (Data Acquisition System) 25, a rotating section controller 26 which controls the X-ray tube 21 or the like being rotated about a body axis of the subject, and a control controller 29 which exchanges control signals or the like with the operation console 1 and the photographing table 10. The beam forming X-ray filter 28 is of an X-ray filter configured so as to be thinnest in thickness as viewed in the direction of X rays directed to the center of rotation corresponding to the center of imaging or scanning, to increase in thickness toward its peripheral portion and to be able to more absorb the X rays. Therefore, the body surface of a subject whose sectional shape is near a circular or elliptic form can be less exposed to radiation. The scan gantry 20 can be tiled about ±30° or so forward and rearward as viewed in the z direction by a scan gantry tilt controller 27.

The X-ray tube 21 and the multi-row X-ray detector 24 are rotated about the center of rotation IC. Assuming that the vertical direction is a y direction, the horizontal direction is an x direction and the travel direction of the table and cradle orthogonal to these is a z direction, the plane at which the X-ray tube 21 and the multi-row X-ray detector 24 are rotated, is an xy plane. The direction in which the cradle 12 is moved, corresponds to the z direction.

Figure 2:
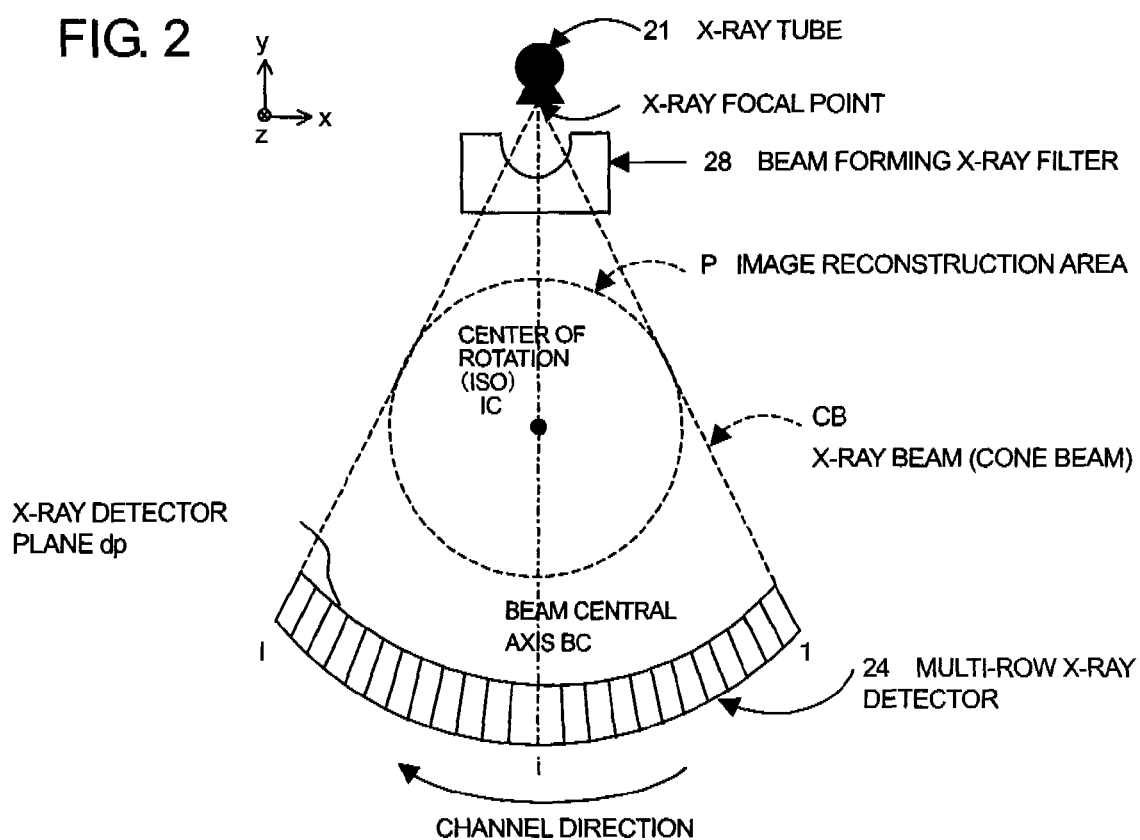
FIG. 2 is an explanatory diagram showing an X-ray generator (X-ray tube) and a multi-row X-ray detector as viewed in an xy plane.
Figure 3:
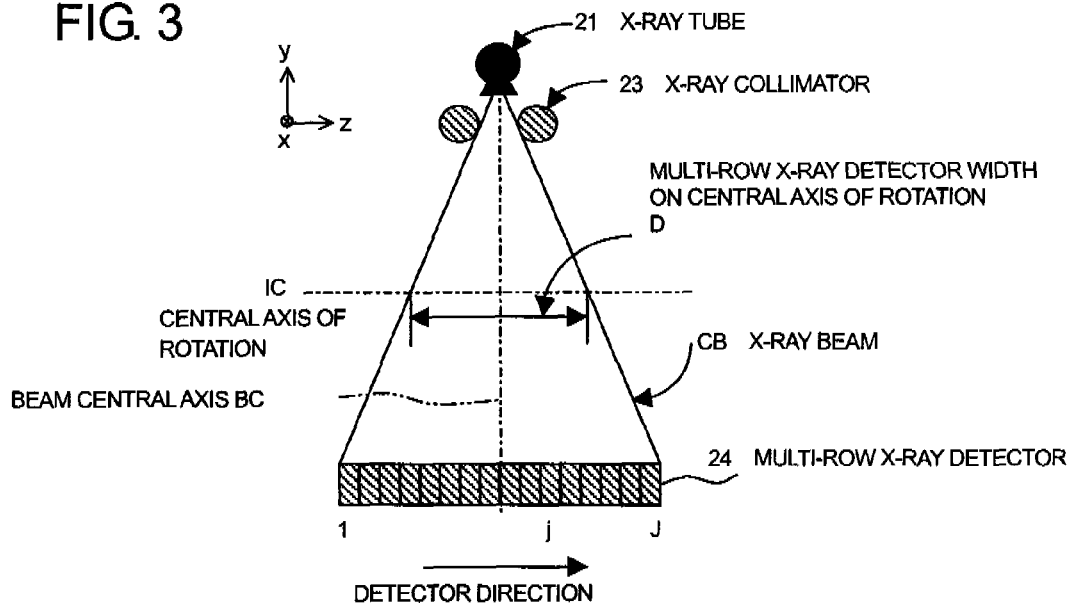
FIG. 3 is an explanatory diagram illustrating the X-ray generator (X-ray tube) and the multi-row X-ray detector as viewed in a yz plane.

FIG. 2 is a diagram showing a geometrical arrangement or layout of the X-ray tube 21 and the multi-row X-ray detector 24 as viewed from the xy plane. FIG. 3 is a diagram showing a geometrical arrangement or layout of the X-ray tube 21 and the multi-row X-ray detector 24 as viewed from the yz plane.

The X-ray tube 21 generates an X-ray beam called a cone beam CB. When the direction of a central axis BC of the cone beam CB is parallel to the y direction, this is defined as a view angle 0°.

The multi-row X-ray detector 24 has X-ray detector rows corresponding to J rows, for example, 256 rows as viewed in the z direction. Each of the X-ray detector rows has X-ray detector channels corresponding to I channels, for example, 1024 channels as viewed in a channel direction.

In FIG. 2, the X-ray beam emitted from the X-ray focal point of the X-ray tube 21 is radiated through the beam forming X-ray filter 28. More X rays are radiated in the center of a reconstruction area or plane P, and less X rays are radiated at a peripheral portion of the reconstruction area P. After the X-ray dose has been controlled spatially, the X rays are absorbed into the subject that exists inside the reconstruction area P, and the X rays transmitted through the subject are acquired by the multi-row X-ray detector 24 as X-ray detector data.

In FIG. 3, the X-ray beam emitted from the X-ray focal point of the X-ray tube 21 is controlled in the direction of a slice thickness of a tomographic image by the X-ray collimator 23. That is, the X-ray beam is controlled in such a manner that the width of the X-ray beam becomes D at a central axis of rotation IC. Then, the X rays are absorbed into the subject existing in the vicinity of the central axis of rotation IC, and the X rays transmitted through the subject are acquired by the multi-row X-ray detector 24 as X-ray detector data.

The projection data acquired by application of the X rays to the subject are A/D converted by the data acquisition system (DAS) 25 through the multi-row X-ray detector 24. Then, the data are inputted to the data acquisition buffer 5 via a slip ring 30. The data inputted to the data acquisition buffer 5 are processed by the central processing unit 3 in accordance with the corresponding program stored in the storage device 7, so that the data are image-reconstructed as a tomographic image, followed by being displayed on the monitor 6. Incidentally, although the present embodiment shows the case in which the multi-row X-ray detector 24 is applied, a two-dimensional X-ray area detector of a matrix structure typified by a flat panel X-ray detector can be applied in an X-ray detector plane dp, and a one-row X-ray detector can further be applied.

Figure 4:
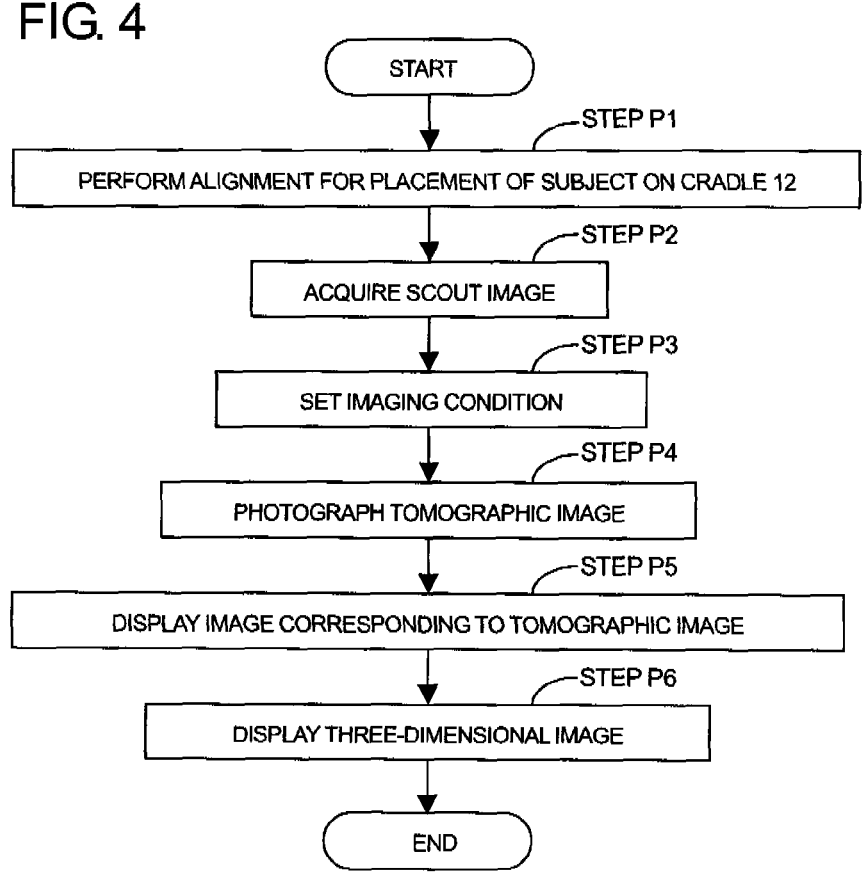
FIG. 4 is a flow chart depicting the flow of subject imaging.

FIG. 4 is a flow chart showing the outline of the operation of the X-ray CT apparatus according to the present embodiment.

At Step P1, the subject is placed on the cradle 12 and its alignment is conducted. A slice light center position of the scan gantry 20 is aligned with a reference point of each region of the subject placed on the cradle 12.

At Step P2, scout image (called also scano image or X-ray penetrated image) acquisition is performed. A scout image can normally be photographed at 0° and 90°. Only a 90° scout image may be photographed or imaged as in the case of, for example, the head, depending upon each region. In the scout image photography, the X-ray tube 21 and the multi-row X-ray detector 24 are fixed and the operation of acquiring X-ray detector data is conducted while the cradle 12 is being linearly moved. The details of the photographing of the scout image will be described later in FIG. 5.

At Step P3, the setting of an imaging or photographing condition is performed while the position and size of a tomographic image to be photographed are being displayed on the scout image. The present embodiment has a plurality of scan patterns such as a conventional scan (axial scan), a helical scan, a variable-pitch helical scan, a helical shuttle scan, etc. The conventional scan is of a scan method for rotating the X-ray tube 21 and the multi-row X-ray detector 24 each time the cradle 12 is axially moved in a z-axis direction at predetermined intervals, thereby acquiring projection data. The helical scan is an imaging method for moving the cradle 12 at a constant velocity while the data acquisition system comprising the X-ray tube 21 and the multi-row X-ray detector 24 are being rotated, thereby acquiring projection data. The variable-pitch helical scan is an imaging method for varying the velocity of the cradle 12 while the data acquisition system comprising the X-ray tube 21 and the multi-row X-ray detector 24 in a manner similar to the helical scan is being rotated, thereby acquiring projection data. The helical shuttle scan is a scan method for accelerating/decelerating the cradle 12 while the data acquisition system comprising the X-ray tube 21 and the multi-row X-ray detector 24 in a manner similar to the helical scan is being rotated, and reciprocating the same in a positive or negative direction of a z axis, thereby acquiring projection data. When these plural photographies are set, the display of X-ray dose information corresponding to once as a whole is conducted. When the number of revolutions or time is inputted, X-ray dose information corresponding to the inputted number of revolutions or the inputted time at its region of interest is displayed upon a cine scan.

At Step P4, tomographic image photography is performed. The details of the tomographic image photography and its image reconstruction will be described in detail later with reference to FIG. 5.

At Step P5, an image-reconstructed tomographic image is displayed.

At Step P6, a three-dimensional image display is performed using each tomographic image sequentially imaged or photographed in the z direction as a three-dimensional image.

Figure 5:
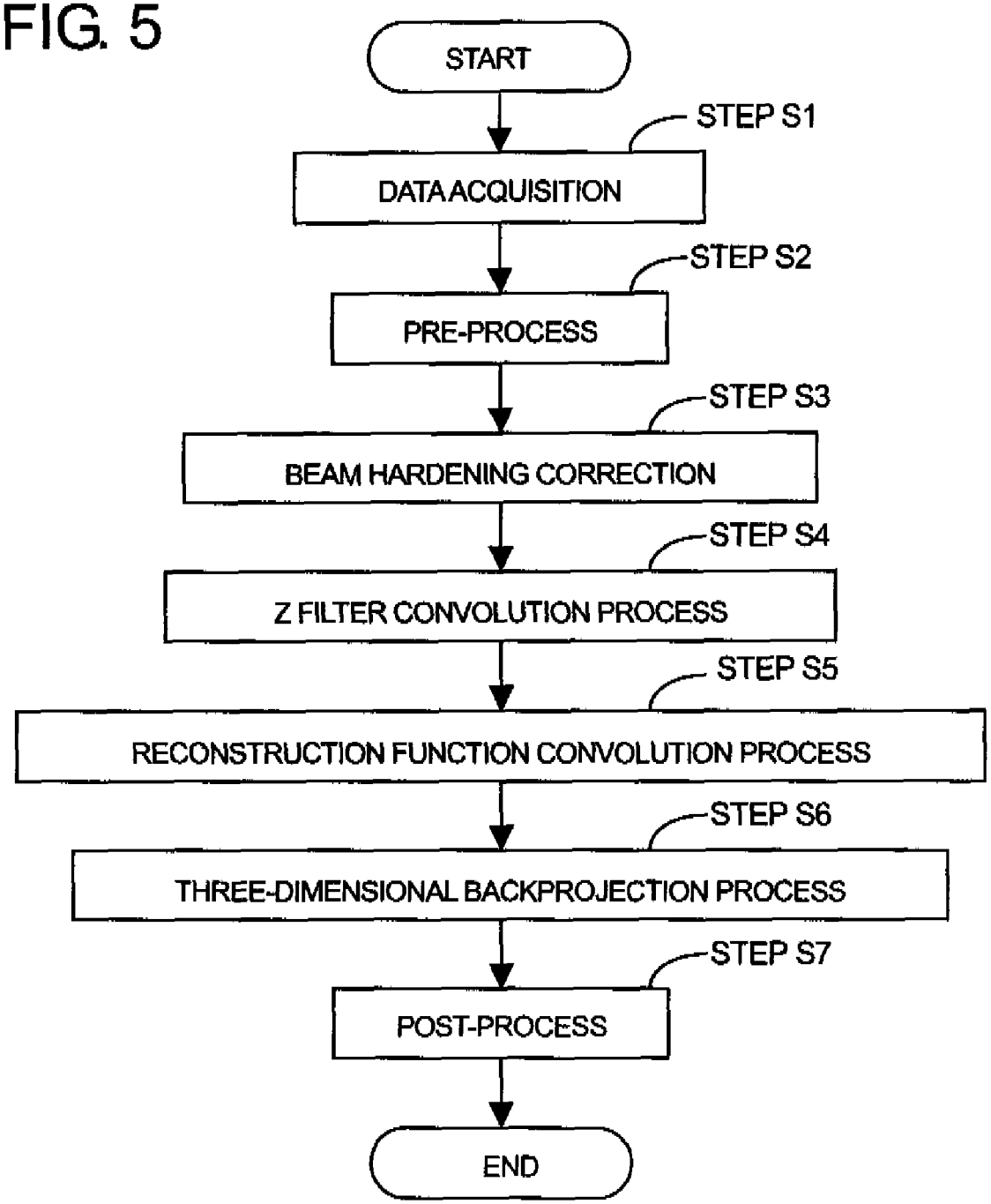
FIG. 5 is a flow chart showing a schematic operation for image reconstruction, of the X-ray CT apparatus according to the one embodiment of the present invention.

FIG. 5 is a flowchart showing the outline of operations for the tomographic image photography and the scout image photography of the X-ray CT apparatus 100 of the present invention.

At Step S1, a helical scan performs the operation of rotating the X-ray tube 21 and the multi-row X-ray detector 24 about the subject and carrying out data acquisition of X-ray detector data while the cradle 12 placed on the imaging or photographing table 10 is being linearly moved, Then, a z-direction coordinate position Ztable (view) is added to X-ray detector data D0 (view, j, i) (where j=1 to ROW, i=1 to CH) indicated by a view angle view, a detector row number j and a channel number i, and data acquisition in a constant-speed range is performed in this condition.

The z-direction coordinate position may be added to X-ray projection data or may be used with being associated with X-ray projection data as another file. When the X-ray projection data is three-dimensionally image-reconstructed upon the helical shuttle scan or the variable-pitch helical scan, information about the z-direction coordinate position is used.

By using it upon the helical scan, conventional scan (axial scan) or cine scan, an improvement in the accuracy of each image-reconstructed tomographic image and an improvement in its image quality can also be realized.

Position control data for the cradle 12 of the photographing table 10 may be used for the z-direction coordinate position. Alternatively, a z-direction coordinate position at each time, which is predicted from an imaging or photographing operation set upon the setting of the imaging condition, can also be used therefor.

Upon the variable-pitch helical scan or helical shuttle scan, data acquisition is performed even at acceleration and deceleration in addition to the data acquisition in the constant-speed range.

Upon the conventional scan (axial scan) or the cine scan, the data acquisition system is rotated once or plural times while the cradle 12 placed on the photographing table 10 is being fixed to a given z-direction position, thereby to perform data acquisition of X-ray detector data. The cradle 12 is moved to the next z-direction position as needed and thereafter the data acquisition system is rotated once or plural times again to perform data acquisition of X-ray detector data.

Upon the scout image photography, the operation of fixing the X-ray tube 21 and the multi-row X-ray detector 24 and performing data acquisition of X-ray detector data while the cradle 12 placed on the photographing table 10 is being linearly moved, is performed.

At Step S2, a pre-process is performed on the X-ray detector data D0 (view, j, i) to convert it into projection data. Upon the pre-process, for example, an offset correction, logarithmic translation, an X-ray dose correction and a sensitivity correction are performed.

If the pre-processed X-ray detector data is displayed upon the scout image photography with each of a pixel size in the channel direction and a pixel size in the z direction corresponding to the linearly traveling direction of the cradle 12 being made coincident with a display pixel size of the monitor 6, then the X-ray detector data is completed as the corresponding scout image.

Next, at Step S3, a beam hardening correction is effected on the pre-processed projection data D1 (view, j, i). Assuming that upon the beam hardening correction of Step S3, projection data subjected to the sensitivity correction of Step S24 at the pre-process S2 is defined as D1 (view, j, i) and data subsequent to the beam hardening correction of Step S3 is defined as D11 (view, j, i), the beam hardening correction of Step S3 is expressed in the form of, for example, a polynomial as given by the following (expression 1). Incidentally, a multiplication arithmetic operation is expressed in "•".

$$D11(\text{view},j,i)=D1(\text{view},j,i)\cdot(B_0(j,i)+B_1(j,i)\cdot D1(\text{view},j,i)+B_2(j,i)\cdot D1(\text{view},j,i)^2) \quad \text{Eq.(1)}$$

Since, at this time, the independent beam hardening corrections can be carried out for every j row of the detectors, the difference between X-ray energy characteristics of the detectors placed for every row can be corrected if X-ray tube voltages of respective data acquisition systems are different on the imaging condition.

At Step S4, a z-filter convolution or overlay process for applying filters in the z direction (row direction) is effected on the projection data D11 (view, j, i) subjected to the beam hardening correction. That is, after the pre-process at each view angle and each data acquisition system, projection data of the multi-row X-ray detector D11 (view, j, i) (where i=1 to CH and j=1 to ROW) subjected to the beam hardening correction is multiplied in the row direction by filters in which such row-direction filter sizes as expressed in the following Equations (2) and (3) are five rows, for example.

$$(w_1(i), w_2(i), w_3(i), w_4(i), w_5(i)) \quad \text{where} \quad \text{Eq. (2)}$$

$$\sum_{k=1}^{5} w_k(i) = 1 \quad \text{Eq. (3)}$$

The corrected detector data D12 (view, j, i) is given as expressed in the following Equation (4):

$$D12(\text{view}, j, i) = \sum_{k=1}^{5} (D11(\text{view}, j+k-3, i) \cdot w_k(j)) \quad \text{Eq. (4)}$$

Incidentally, assuming that the maximum value of the channel is CH and the maximum value of the row is ROW, the following Equations (5) and (6) are established.

$$D11(\text{view},-1,i)=D11(\text{view},0,i)=D11(\text{view},1,i) \quad \text{Eq. (5)}$$

$$D11(\text{view},\text{ROW},i)=D11(\text{view},\text{ROW}+1,i)=D11(\text{view},\text{ROW}+2,i) \quad \text{Eq. (6)}.$$

When row-direction filter coefficients are changed for every channel, the slice thickness can be controlled depending on the distance from an image reconstruction center. In a tomographic image, its peripheral portion generally becomes thicker in slice thickness than the reconstruction center thereof. Therefore, the row-direction filter coefficients are changed at the central and peripheral portions, thereby making it possible to make the slice thickness substantially uniform even at the peripheral portion and the image reconstruction center. For example, when the row-direction filter coefficients are changed at the central portion and the peripheral portion so as to widely change in width in the neighborhood of a central channel and narrowly change in width in the neighborhood of a peripheral channel, the slice thickness can be made substantially uniform even at the peripheral portion and the image reconstruction center.

Controlling the row-direction filter coefficients at the central and peripheral channels of the multi-row X-ray detector 24 in this way makes it possible to control the slice thicknesses at the central and peripheral portions. Thickening the slice thickness slightly by each row-direction filter yields extensive improvements in both artifact and noise. Thus, the degree of the improvement in artifact and the degree of the improvement in noise can also be controlled. That is, it is possible to control a three-dimensionally image-reconstructed tomographic image, i.e., image quality in the xy plane. In addition to above, a tomographic image having a thin slice thickness can also be realized by setting row-direction (z-direction) filter coefficients to deconvolution filters as another embodiment.

At Step S5, a reconstruction function convolution process is performed. That is, projection data is subjected to Fourier transform for transforming the projection data to a frequency region or domain and multiplied by a reconstruction function, followed by being subjected to inverse Fourier transform. Assuming that upon the reconstruction function convolution process S5, projection data subsequent to the z filter convolution process is defined as D12, projection data subsequent to the reconstruction function convolution process is defined as D13, and the convoluting reconstruction function is defined as Kernel (j), the reconstruction function convolution process is expressed as given by the following Equation (7). Incidentally, a convolution arithmetic operation is expressed in "*" in the present embodiment.

$$D13(view, j, i) = D12(view, j, i) * Kernel(j) \quad \text{Eq. (7)}$$

That is, since the independent reconstruction function convolution process can be performed for every j row of the detectors, the reconstruction function Kernel (j) can correct differences in noise characteristic and resolution characteristic for every row.

At Step S6, a three-dimensional backprojection process is performed on the projection data D13 (view, j, i) subjected to the reconstruction function convolution process to determine backprojection data D3 (x, y, z). An image-reconstructed image is three-dimensionally image-reconstructed on an xy plane corresponding to a plane orthogonal to the z axis. A reconstruction area or plane P to be shown below is assumed to be parallel to the xy plane.

At Step S7, a post-process such as image filter convolution, CT value conversion or the like is effected on the backprojection data D3 (x, y, z) to obtain a tomographic image D31 (x, y).

Assuming that upon the image filter convolution process in the post-process, a tomographic image subsequent to the three-dimensional backprojection is defined as D31 (x, y, z), data subsequent to the image filter convolution is defined as D32 (x, y, z), and a two-dimensional image filter convolved on the xy plane corresponding to a tomographic image plane is defined as Filter (z), the following Equation (8) is established.

$$D32(x, y, z) = D31(x, y, z) * \text{Filter}(z) \quad \text{Eq. (8)}$$

That is, since the independent image filter convolution process can be performed for every tomographic image at respective z-coordinate positions, it is possible to correct differences in noise characteristic and resolution characteristic for every row.

Alternatively, an image space z-direction filter convolution process shown below may be performed after the two-dimensional image filter convolution process. The image space z-direction filter convolution process may be performed before the two-dimensional image filter convolution process. Further, a three-dimensional image filter convolution process may be performed to bring about such an effect as to share both the two-dimensional image filter convolution process and the image space z-direction filter convolution process.

Assuming that upon the image space z-direction filter convolution process, a tomographic image subjected to the image space z-direction filter convolution process is defined as D33 (x, y, z), and a tomographic image subjected to the two-dimensional image filter convolution process is defined as D32 (x, y, z), the following (expression 9) is established. However, v(i) becomes such a coefficient row as expressed below (in expression 10) in the form of image space z-direction filter coefficients at which the width in the z direction is 2l+1.

$$D32(x, y, z) = D32(x, y, z+i) \sum_{i=-l}^{l} v(i) \quad \text{Eq. (9)}$$

$$v(-l), v(-l+1), \ldots v(-1), v(0), v(1), \ldots v(l-1), v(l) \quad \text{Eq. (10)}$$

Upon the helical scan, the image space filter coefficient v(i) may be an image space z-direction filter coefficient independent on a z-direction position. However, particularly when the conventional scan (axial scan) or cine scan is performed using the two-dimensional X-ray area detector 24 or the multi-row X-ray detector 24 or the like broad in detector width as viewed in the z direction, the image space z-direction filter coefficient v(i) may preferably make use of an image space z-direction filter coefficient dependent on the position of the row of the X-ray detector in the z direction. This is because it is further effective since detailed adjustments dependent on row positions of respective tomographic images can be made.

The so-obtained tomographic images are displayed on the monitor 6.

Embodiments using the X-ray CT apparatus will be shown below.

The present embodiment shows an embodiment in which an X-ray penetration path length corresponding to a profile distribution of a subject is determined using a scout image or X-ray projection data thereof, and imaging conditions for an X-ray tube voltage (80 kV, for example) lower than each of geometrical characteristic amounts of the profile distribution of the subject and an X-ray tube voltage (140 kV, for example) higher than it are set up or established. Described specifically, of the imaging conditions, an X-ray tube current is defined so as to be optimized, and an image noise index value corresponding to an index value of the quality of each of tomographic images at the low X-ray tube voltage and the high X-ray tube voltage is defined as a value set in advance.

Figure 12:
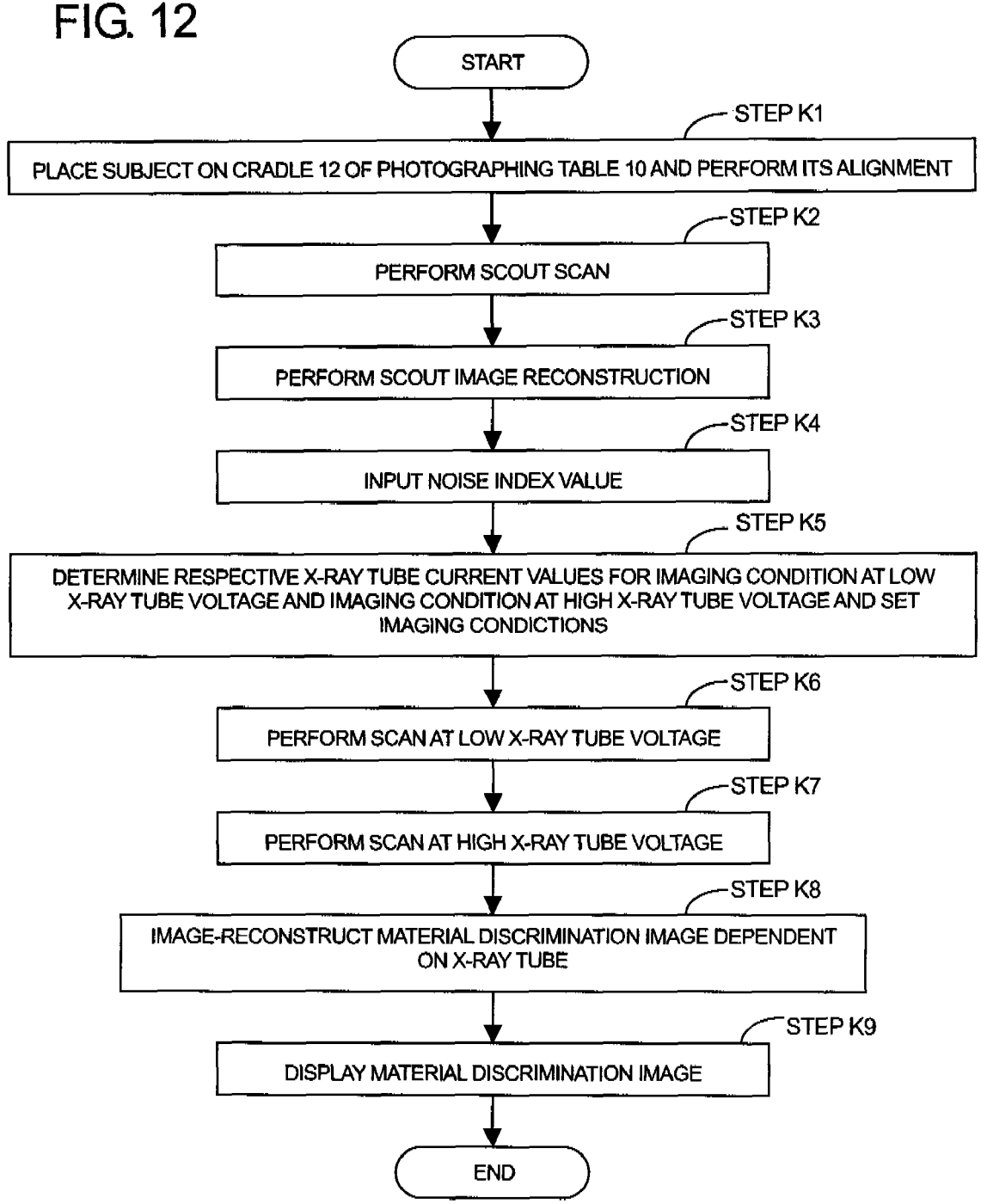
FIG. 12 is a flow chart used where imaging conditions for two types of X-ray tube voltages are determined using a scout image.

FIG. 12 is a flow chart used where imaging conditions for two types of X-ray tube voltages are determined using a scout image according to the present embodiment.

At Step K1, the subject is placed on the cradle 12 of the photographing table 10 and its alignment is conducted.

At Step K2, a scout scan is performed.

At Step K3, scout image reconstruction is conducted.

At Step K4, a noise index value is inputted.

At Step K5, respective X-ray tube current values for an imaging condition at a low X-ray tube voltage and an imaging condition at a high X-ray tube voltage are determined to set the imaging conditions.

At Step K6, a scan at the low X-ray tube voltage is performed.

At Step K7, a scan at the high X-ray tube voltage is performed.

At Step K8, a material discrimination image dependent on the X-ray tube is image-reconstructed.

At Step K9, the material discrimination image is displayed.

At Step K5, geometrical characteristic amounts of a profile distribution, including a profile area, ellipticity at the time that a profile distribution is elliptically made approximate, are determined from a profile distribution of each z-direction coordinate position of the subject, based on the scout image determined at Step K3. Thus, variables for imaging conditions for controlling image noise containing X-ray tube current are controlled under a tomographic imaging condition at a low X-ray tube voltage and a tomographic imaging condition at a high X-ray tube voltage, using an automatic X-ray exposure mechanism in such a manner that a tomographic image at a low X-ray tube voltage and a tomographic image at a high X-ray tube voltage become identical in image quality, that is, they become the same image size (standard deviation of each pixel), thereby making it possible to optimize the image quality.

Incidentally, the motion of the automatic X-ray exposure mechanism at this time is shown below.

An embodiment which can set the optimum imaging conditions at the respective z-direction coordinate positions using the geometrical characteristic amounts of the profile distribution of the subject such that uniform image quality is taken in the z direction by the automatic X-ray exposure mechanism and which can perform a reduction in exposure and an improvement in image quality by executing the imaging conditions, will be shown below.

Figure 13:
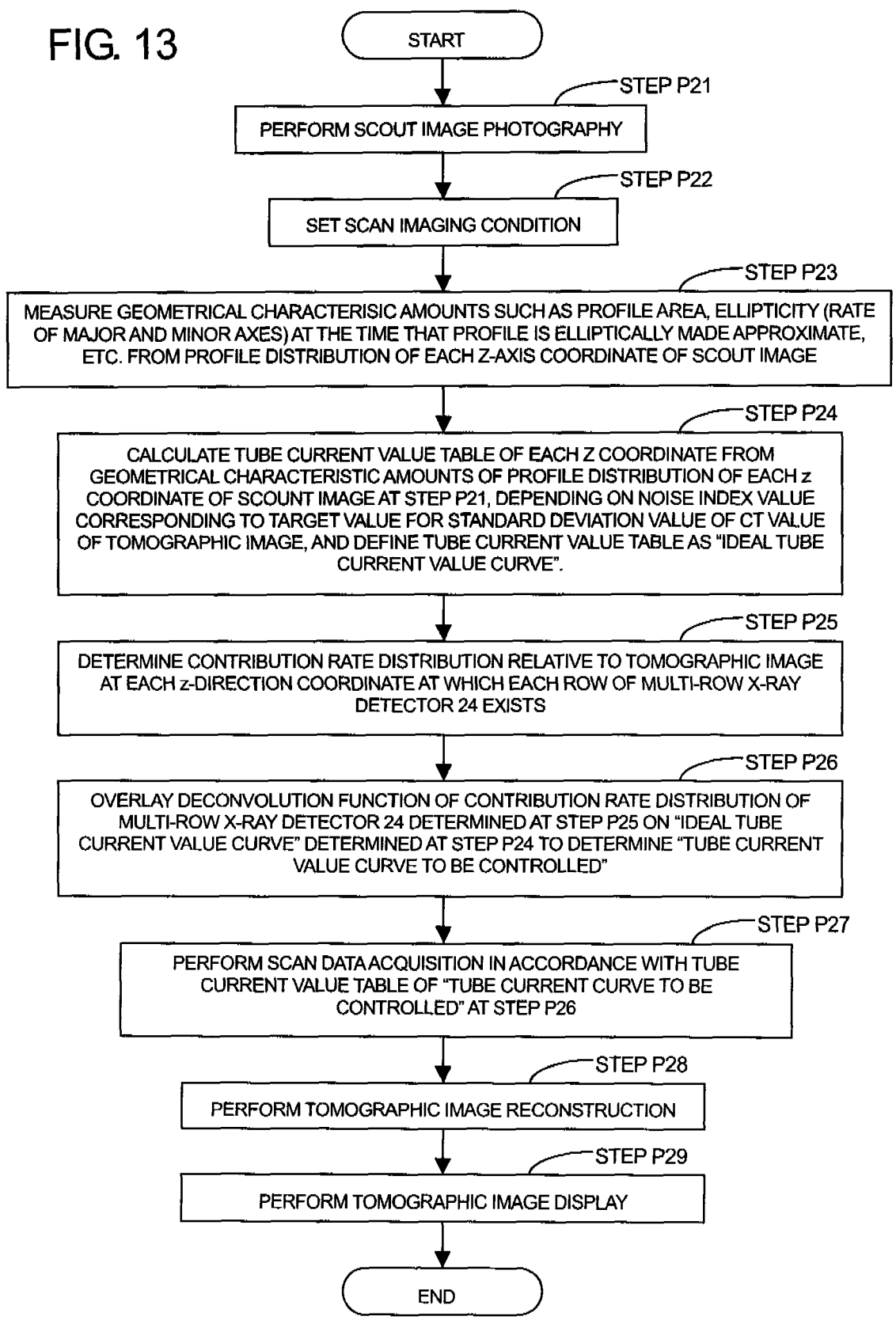
FIG. 13 is a flow chart used where imaging conditions for two types of X-ray tube voltages are determined using a scout image by a helical scout scan.

The flow of an embodiment that obtains a scout image and sets the optimum X-ray tube current at each z-direction coordinate position such that uniform image quality is taken in the z direction, will be shown in FIG. 13 to be illustrated below.

In the following embodiment, Steps P25, P26 and P27 to be described later are conducted in consideration of an influence due to the z-direction width of each X-ray detector in the case of a multi-row X-ray detector. When it is however not necessary to take into consideration the z-direction width of the X-ray detector due to such reasons as described in the following description, imaging condition setting may be performed at Step P27 or X-ray projection data acquisition may be performed, based on "ideal tube current curve" determined at Step P24 without executing processes of Steps P25 and P26.

The z-direction width of the X-ray detector is not so wide.

A z-direction change in the subject is smaller than the z-direction width of the X-ray detector.

The accuracy of determining uniformity of image quality in the z direction is not strict.

The overall operation and the flow of processing will be explained below using FIG. 13.

At Step P21, scout image photography by a helical scout scan is performed.

At Step P22, a scan imaging condition is set.

At Step P23, geometrical characteristic amounts such as a profile area, ellipticity (rate of major and minor axes) at the time that a profile distribution is elliptically made approximate, etc. are measured from a profile distribution of respective z-axis coordinates of the scout image.

At Step P24, a tube current value table of each z coordinate is calculated from geometrical characteristic amounts of a profile distribution of each z coordinate of the scout image at Step P21, depending on a noise index value corresponding to a target value for a standard deviation value of a CT value of a tomographic image. This tube current value table will be defined as "ideal tube current value curve" as shown in FIG. 15A.

At Step P25, a contribution rate distribution relative to a tomographic image at each z-direction coordinate at which each row of the multi-row X-ray detector 24 exists, is determined as shown in FIG. 15C.

At Step P26, a deconvolution function of the contribution rate distribution of the multi-row X-ray detector 24, which has been determined at Step P25, is overlaid on the "ideal tube current value curve" determined at Step P24 thereby to determine a "tube current value curve to be controlled" as shown in FIG. 15D.

At Step P27, scan data acquisition is performed in accordance with the tube current value table of "tube current curve to be controlled" at Step P26.

At Step P28, tomographic image reconstruction is carried out.

At Step P29, a tomographic image display is conducted.

The relationship between a standard deviation value of a CT value corresponding to each index value of image noise and a plurality of characteristic parameters of a profile distribution of each scout image in a region of interest of a typical portion of a tomographic image set every region of the subject is determined in advance. That is, the subject is aligned in the z direction and thereafter the relations between noise index values of respective tomographic image positions dependent on z-direction coordinates, geometrical characteristic amounts of a profile distribution of each scout image or X-ray projection data thereof, and X-ray tube current values used in imaging may be associated with one another in advance.

Figure 14:
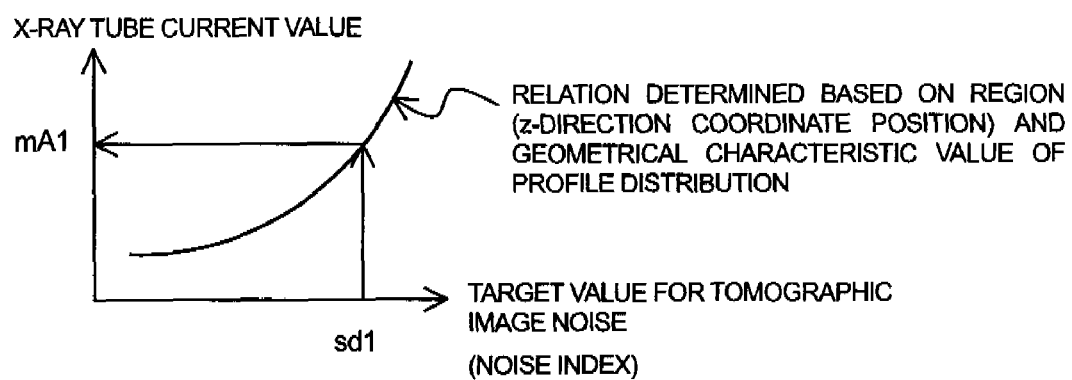
FIG. 14 is a diagram showing the relationship between a target value for image noise and an X-ray tube current value.
Figure 16:
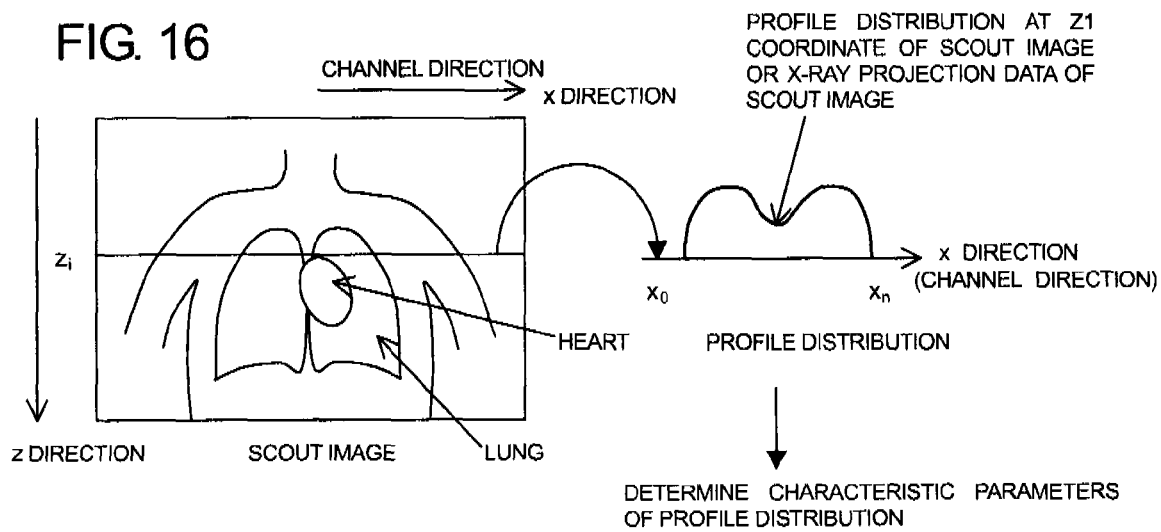
FIG. 16 is a diagram depicting geometrical characteristic amounts of a profile distribution.

Characteristic parameters of a profile distribution of the acquired scout image or projection data thereof are determined based on these relation expressions. Thereafter, if as shown in FIG. 16, a plurality of geometrical characteristic amounts of the profile distribution and each region corresponding to a z-direction coordinate position of a subject are determined, and a noise index value corresponding to a target value of image noise is designated, then each X-ray tube current value to be controlled is determined. Thus, an X-ray tube current value corresponding to each z-coordinate value can be determined along the z direction of the scout image as shown in FIG. 14, and an X-ray tube current value curve (X-ray tube current value table) extending along the z direction is determined.

In the case of an X-ray detector having one row or an X-ray detector reduced in the number of rows, a helical scan or a conventional scan (axial scan) or a cine scan at plural positions as viewed in the z direction, or a variable-pitch helical scan or a helical shuttle scan is performed while each X-ray tube current value is being changed along the z direction while the X-ray tube current value table is being held as it is, whereby a CT-value standard deviation value of a tomographic image at each z-direction position could be held approximately constant.

Since, however, the detector width is wide in the z direction in the multi-row X-ray detector of matrix structure or the two-dimensional X-ray area detector, projection data three-dimensionally backprojected onto a tomographic image at a given z-direction coordinate position exists at plural z-direction positions in dispersed form. Therefore, when the helical scan or the conventional scan (axial scan) or the cine scan at the plural positions in the z direction is performed while each X-ray tube current value is being changed along the z direction with the X-ray tube current value table held as is, where the multi-row X-ray detector or the two-dimensional X-ray area detector is used, there is a fear that a CT-value standard deviation of a tomographic image, corresponding to the index of image noise is not controlled properly as shown in FIG. 15B because a contributory z-direction width of each detector is wide, so that it expands in the z direction, thus causing blurring.

In order to avoid it, a distribution of a rate of contribution of each detector row to a tomographic image at a certain or given z-direction position is determined along the z direction as shown in FIG. 15C. This contribution-rate distribution differs according to a helical pitch, how to multiply weight coefficients of respective detector rows at the image reconstruction, scan's modes (helical scan, conventional scan (axial scan) or cine scan), etc.

If a deconvolution function of the distribution of the distribution rate distributed in the z direction is determined and overlaid on its corresponding "X-ray tube current value curve" (X-ray tube current value table), that is, each z-direction filter is applied with a tendency toward high-frequency emphasis, so that a "tube current value curve to be controlled" is determined. If the helical scan, the conventional scan (axial scan) or the cine scan is performed while the X-ray tube current value is being changed along the z direction, and image reconstruction is performed, as shown in the "tube current value curve to be controlled" (tube current value table to be controlled), then the high-frequency emphasized tube current value curve is smoothed in the z direction at the contribution rate distributed in the z direction, and image noise (standard deviation of CT value) of a tomographic image that could obtain just right can be made substantially uniform in the z direction as shown in FIG. 15D.

The geometric characteristic amounts of the profile distribution at each z-axis coordinate of the scout image determined at Step P21, or ones shown below like FIG. 16, or characteristic parameters determined by calculating or computing them in combination are considered. For example, a profile area may be calculated using Equation (11) as shown.

$$\text{Profile area} = \sum_{i=x_0}^{x_n} Prf(x) \quad \text{Eq. (11)}$$

Moreover, a circular degree of profile distribution may be calculated using Equation (12) as shown below.

$$\text{Circular degree of profile distribution} = \quad \text{Eq. (12)}$$
$$\frac{1}{4\pi} \frac{(\text{profile circumference length})^2}{\text{profile area}}$$

Furthermore, lengths of minor and major axes may be calculated at the time that a profile distribution is made approximate to a single ellipse. In addition, calculations may be made for respective lengths of a minor axis 1, a major axis 1 through a minor axis N and a major axis N at the time that a profile distribution is made approximate to a plurality of (N) ellipses, and a number of labels of profile distribution, i.e., number of sequential regions, may be determined.

Figure 17A:
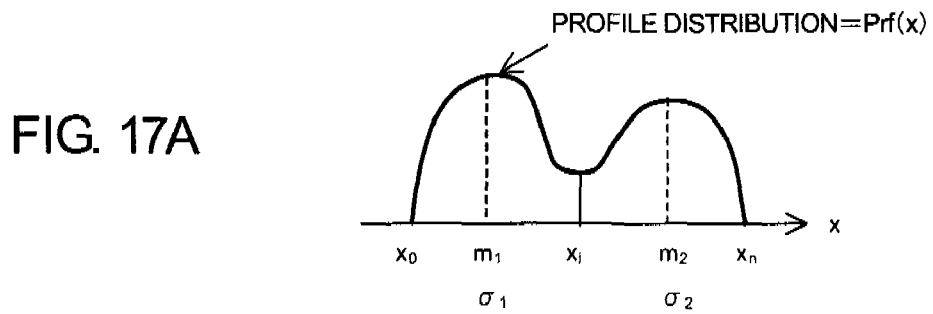
FIG. 17A is an independent profile distribution.
Figure 17B:
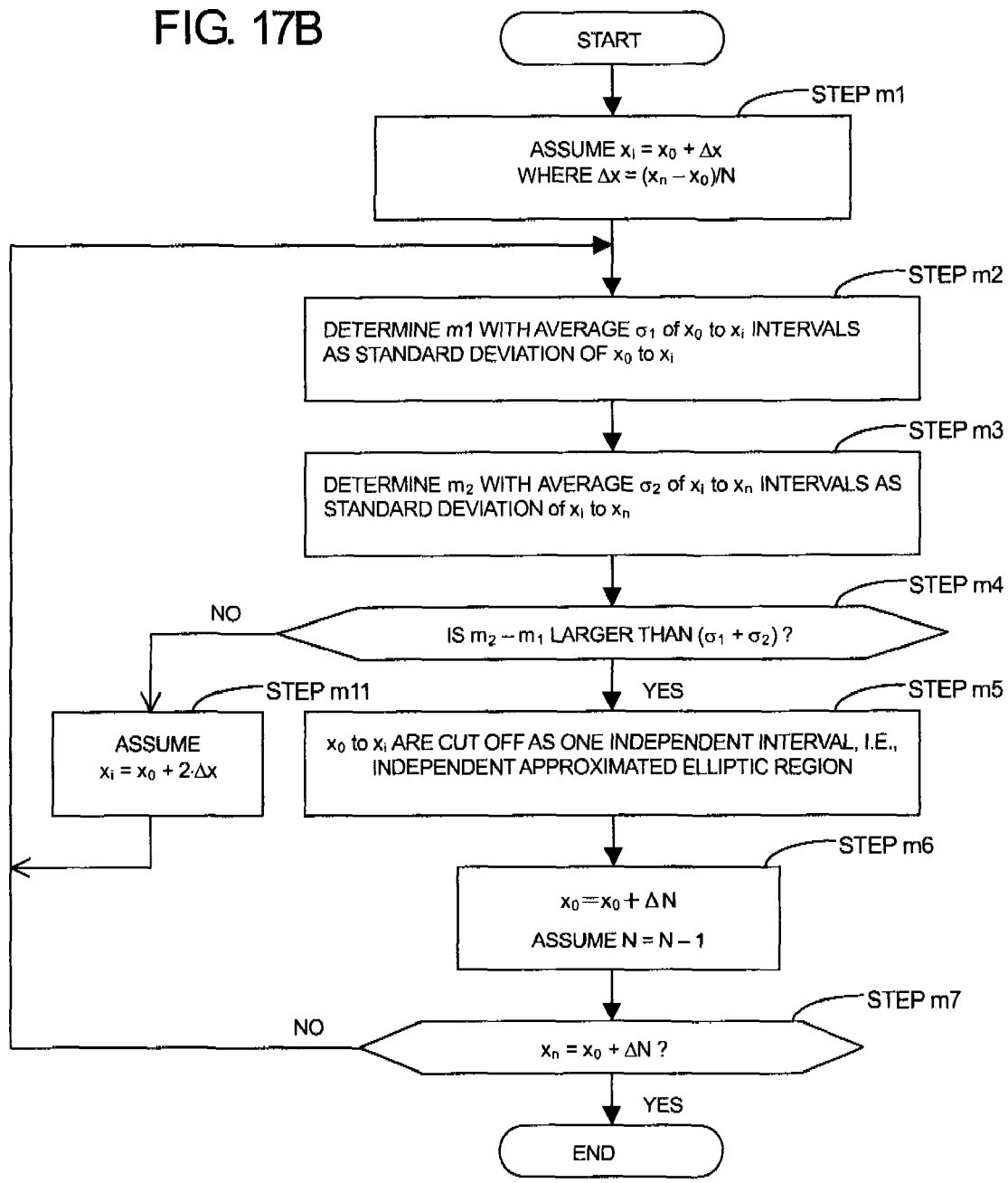
FIG. 17B is a flow chart showing the flow of a process for determining the extraction of the independent profile distribution shown in FIG. 17A.

A flow chart showing a decision as to whether the profile distribution at the fourth item referred to above should be divided into the plural ellipses, that is, independent profiles should be extracted, is shown in FIG. 17B. Referring to both FIGS. 17A and 17B, at Step m1, $x_i = x_0 + \Delta x$. However, $\Delta x = (x_n - x_0)/N$.

At Step m2, $m_1$ is determined with the average $\sigma_1$ of $x_0$ to $x_i$ intervals as a standard deviation of $x_0$ to $x_i$.

At Step m3, $m_2$ is determined with the average $\sigma_2$ of $x_i$ to $x_n$ intervals as a standard deviation of $x_i$ to $x_n$ as shown in Equation (13) below.

$$(m_2 - m_1) > K \cdot \frac{N}{2} \cdot (\sigma_1 + \sigma_2) \quad \text{Eq. (13)}$$

However, K can be judged concretely so as to be a suitable coefficient.

At Step m4, it is determined that $(m_2 - m_1)$ is sufficiently larger than $(\sigma_1 + \sigma_2)$. If the answer is found to be YES, then the flow chart proceeds to Step m5. If the answer is found to be NO, then the flow chart proceeds to Step m11.

A Step m5, $x_0$ to $x_i$ are treated as one independent section or interval and assumed to be another profile distribution from $x_i$ to $x_n$. That is, $x_0$ to $x_i$ are divided as independent regions and made approximate to elliptic form, followed by being cut off as other approximate elliptic regions. Described specifically, there are considered where tomographic images for both feet are seen upon the imaging or photography of the leg portions of the subject, or where the chest and dropped two arms are seen, etc.

At Step m6, $x_0 = x_0 + \Delta N$ and $N = N - 1$.

At Step m7, it is determined whether $x_n = x_0 + \Delta N$. If the answer is found to be YES, then the flow chart is terminated. If the answer is found to be NO, then the flow chart proceeds to Step m2.

At Step m11, $x_i = x_0 + 2\Delta x$.

It is determined based on such a judgement whether the profile distribution is divided into the plural elliptic approximations.

At each z-coordinate position referred to above, the imaging conditions such as the optimum X-ray tube current at each z-coordinate position can be determined according to each profile distribution, based on the geometrical characteristic parameters, each parameter at the elliptic approximation corresponding to its one, etc. Since the elliptic approximation is made at each z-coordinate position, a projection data length (called also penetration path length) of an ellipse approximated in each view direction as shown in FIGS. 20A and 20B changes when each view direction of the data acquisition system is taken into consideration as shown in FIGS. 18A-C and 19A-C, and according to Equations (14) and (15) shown below.

$$\left(\frac{x}{a_1}\right)^2 + \left(\frac{y}{b_1}\right)^2 = 1 \quad \text{Eq. (14)}$$

$$r(\theta) = (a_1^2 \cdot \cos^2\theta + b_1^2 \cdot \sin^2\theta)^{1/2} \quad \text{Eq. (15)}$$
$$= (b_1^2 + (a_1^2 - b_1^2) \cdot \cos^2\theta)^{1/2}$$
$$= \left(b_1^2 + (a_1^2 - b_1^2) \cdot \left(\frac{1 + \cos^2\theta}{2}\right)\right)^{1/2}$$

Thus, if the physical or position relationship between each view direction of the data acquisition system and each ellipse made approximate from the profile distribution is taken into consideration, then the optimum X-ray tube current value is reduced and a reduction in exposure is enabled.

Figure 19A:
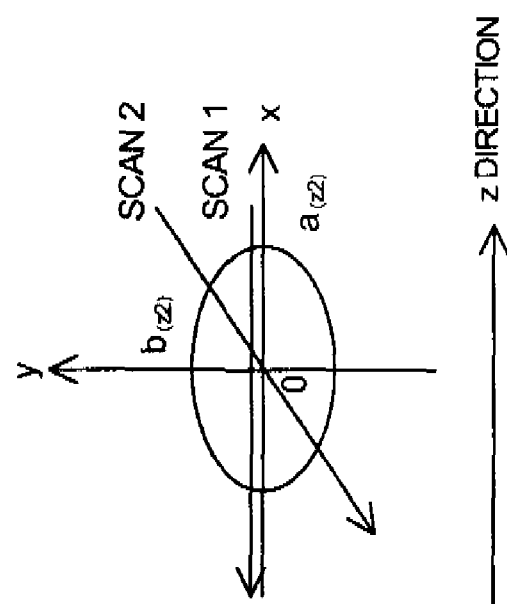
FIGS. 19A, 19B, and 19C are diagrams illustrating a case in which approximated ellipses differ according to z-direction coordinate positions in the case of a helical scan.
Figure 19B:
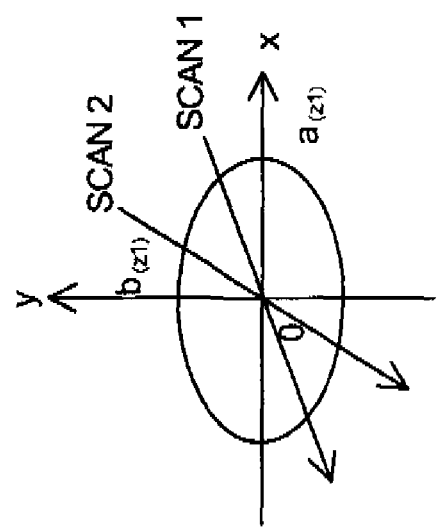
Figure 19C:
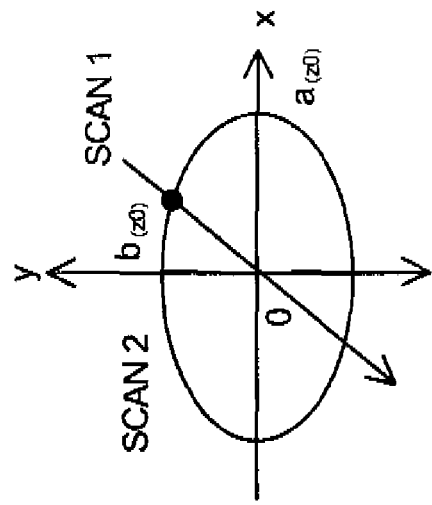
Figure 20A:
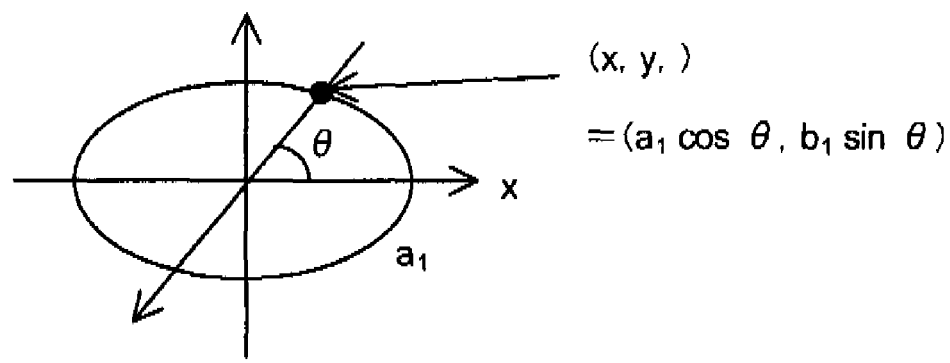
FIGS. 20A and 20B are diagrams showing a projection data length in a θ direction in the case of an elliptic approximation.
Figure 20B:
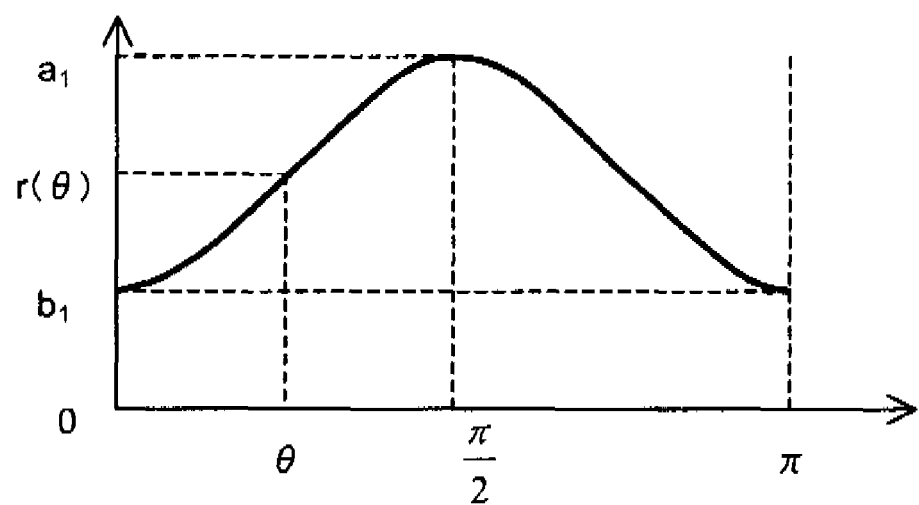

Although the ellipses approximated in the view direction of the data acquisition system remain unchanged at the conventional scan (axial scan) or the cine scan as shown in FIGS. 18A, 18B, and 18C, the ellipses approximated as the z-direction coordinate moves, change at the helical scan as shown in FIGS. 19A, 19B, and 19C, and the optimum X-ray tube current value set for each view direction of the data acquisition system also changes.

Namely, if both scans 1 and 2 are identical in view direction at the conventional scan (axial scan) or cine scan shown in FIGS. 18A, 18B, and 18C, then the same optimum X-ray tube current value is reached. At the helical scan of FIGS. 19A, 19B, and 19C, however, the z-direction coordinate positions are also shifted when the view direction is shifted depending on the scans 1 and 2, so that the sizes of approximated ellipses also differ and the optimum X-ray tube current values become different. A reduction in exposure can be further improved by taking into consideration the view direction in this way.

Thus, the variables for imaging conditions for controlling image noise containing X-ray tube currents for an imaging condition at a low X-ray tube voltage and an imaging condition at a high X-ray tube voltage are changed by the automatic X-ray exposure mechanism thereby to make it possible to optimize image quality.

In the present embodiment, the X-ray tube voltage (X-ray tube voltage of 120 kV, for example) and X-ray tube voltages for tomographic image photography at the low X-ray tube voltage (X-ray tube voltage of 80 kV, for example) and tomographic image photography at the high X-ray tube voltage (X-ray tube voltage of 140 kV, for example) are different.

Namely, there is considered where since the X-ray energy distributions (X-ray quality distributions) differ every X-ray tube voltage, the profile distributions of the subject every X-ray tube voltage differ even though the same subject is photographed, due to the influence of the X-ray beam hardening. Incidentally, the profile distribution indicates the X-ray penetration path length of the subject.

Figure 21:
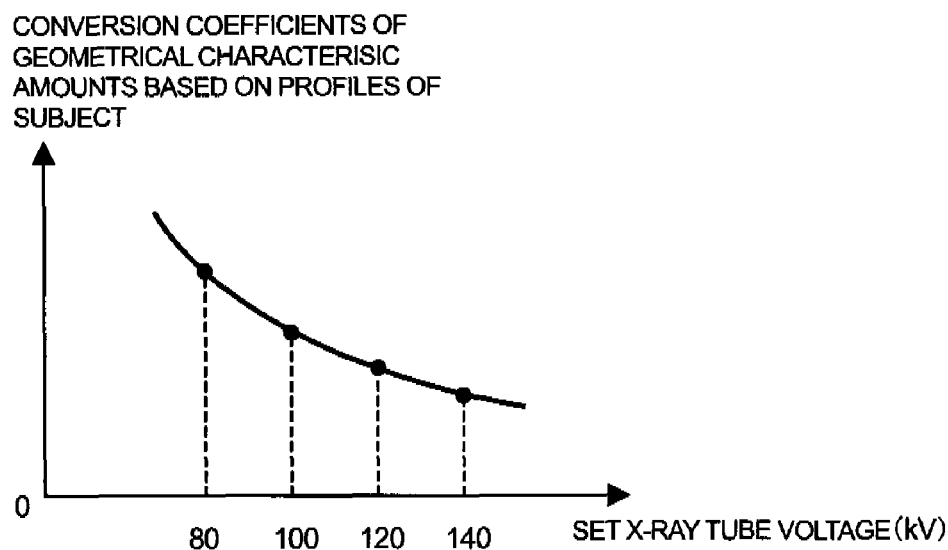
FIG. 21 is a diagram depicting the dependence of geometrical characteristic amounts on each X-ray tube voltage.

In this case, there is a need to convert the geometrical characteristic amounts determined from the subject's profile distribution obtained from the scout image or the X-ray projection data acquired from the scout image by conversion coefficients as shown in FIG. 21.

When the tomographic image photography is performed at another X-ray tube voltage with the X-ray tube voltage 120 kV of the scout image as 1.0 in FIG. 21, geometrical characteristic amounts determined from the subject's profile distribution with being multiplied by correction coefficients are converted.

Thus, the optimum X-ray imaging conditions based on noise index values at the respective X-ray tube voltages are determined.

Consequently, the tomographic image photography at the low X-ray tube voltage and the tomographic image photography at the high X-ray tube voltage at Steps K6 and K7 of FIG. 12 can be carried out respectively.

At Step K8 of FIG. 12, images in which materials X and Y are discriminated are obtained by the following calculations. That is, in this case, distributions indicative of the existence of the materials X and Y can be imaged by bringing tube voltage dependent information about X-ray absorption coefficients different every atom into imaging.

Figure 22:
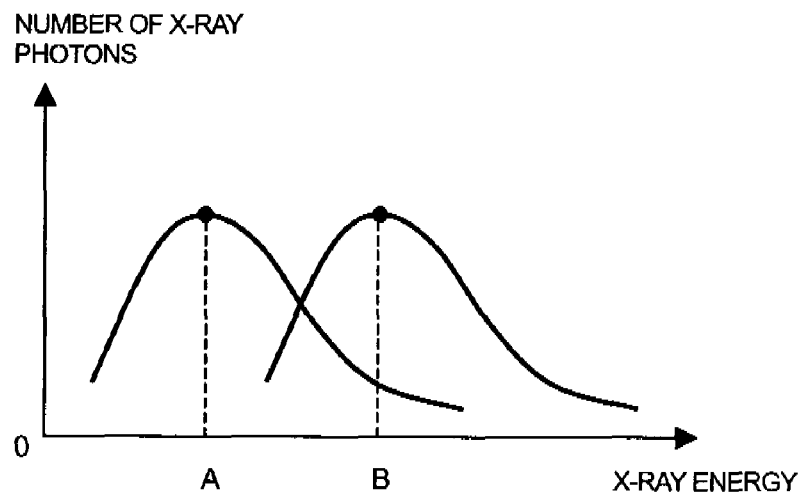
FIG. 22 is a diagram showing X-ray quality distributions having effective energy A and B respectively.

As to two types of tomographic images different in X-ray quality, i.e., X-ray tube voltage's energy, two different tomographic images having energy characteristics indicative of the dependence of X-ray absorption coefficients corresponding to effective energies A and B on X-ray tube voltages respectively are obtained as shown in FIG. 22. Distribution images having energy characteristics indicative of the dependence of quantitative X-ray absorption coefficients related to desired materials on X-ray tube voltages can be determined by calculation from a tomographic image image-reconstructed from X-ray projection data based on X rays having the energy A and a tomographic image image-reconstructed from X-ray projection data based on X rays having the energy B.

A CT value at the tomographic image image-reconstructed from the projection data based on the X rays having the energy A, and a CT value at the tomographic image image-reconstructed from the projection data based on the X rays having the energy B are respectively given by the following Equations (16) and (17):

$$CT_A = \alpha_A X + \beta_A Y + \gamma_A \qquad \text{Eq. (16)}$$

$$CT_B = \alpha_B X + \beta_B Y + \gamma_B \qquad \text{Eq. (17)}$$

Here, X and Y respectively indicate the amount of a desired material (unknown quantity). $\alpha_A$, $\alpha_B$, $\beta_A$, $\beta_B$, $\gamma_A$ and $\gamma_B$ are respectively constants found out by measurement in advance.

X and Y are respectively determined from such CT values by the following Equations (18) and (19):

$$X = \frac{(CT_A - \gamma_A)\beta_B - (CT_B - \gamma_B)\beta_A}{\alpha_A \beta_B - \alpha_B \beta_A} \qquad \text{Eq. (18)}$$

$$Y = \frac{(CT_A - \gamma_A)\alpha_B - (CT_B - \gamma_B)\alpha_A}{\alpha_B \beta_A - \alpha_A \beta_B} \qquad \text{Eq. (19)}$$

Thus, an image about X and an image about Y are respectively formed. X and Y are for example, calcium, fat, iron, etc. The quantitative distribution image of each desired material can be obtained from the two tomographic images different in X-ray quality.

That is, the Equations (18) and (19) are rewritten into the following Equation (20):

$$\begin{pmatrix} CT_A \\ CT_B \end{pmatrix} = \begin{pmatrix} \alpha_A & \beta_A \\ \alpha_B & \beta_B \end{pmatrix} \begin{pmatrix} X \\ Y \end{pmatrix} + \begin{pmatrix} \gamma_A \\ \gamma_B \end{pmatrix} \qquad \text{Eq. (20)}$$

Thus, the following Equation (21) is obtained.

$$\begin{pmatrix} X \\ Y \end{pmatrix} = \begin{pmatrix} \alpha_A & \beta_A \\ \alpha_B & \beta_B \end{pmatrix}^{-1} \begin{pmatrix} CT_A \\ CT_B \end{pmatrix} + \begin{pmatrix} \alpha_A & \beta_A \\ \alpha_B & \beta_B \end{pmatrix}^{-1} \begin{pmatrix} \gamma_A \\ \gamma_B \end{pmatrix} \qquad \text{Eq. (21)}$$

That is, the materials X and Y are obtained as expressed in the following Equations (22) and (23):

$$X = w1 \cdot CT_A + w2 \cdot CT_B + c1 \qquad \text{Eq. (22)}$$

$$Y = w3 \cdot CT_A + w4 \cdot CT_B + c2 \qquad \text{Eq. (23)}$$

However, w1, w2, w3, w4, c1 and c2 at this time are given by the following Equations (23) through (29):

$$w1 = \frac{\beta_B}{\alpha_A \beta_B - \alpha_B \beta_A} \qquad \text{Eq. (24)}$$

$$w2 = \frac{-\beta_A}{\alpha_A \beta_B - \alpha_B \beta_A} \qquad \text{Eq. (25)}$$

$$w3 = \frac{\alpha_B}{\alpha_B \beta_A - \alpha_A \beta_B} \qquad \text{Eq. (26)}$$

$$w4 = \frac{-\alpha_A}{\alpha_B \beta_A - \alpha_A \beta_B} \qquad \text{Eq. (27)}$$

$$C1 = \frac{-\beta_B \gamma_A + \beta_A \gamma_B}{\alpha_A \beta_B - \alpha_B \beta_A} \qquad \text{Eq. (28)}$$

$$C2 = \frac{-\beta_B \gamma_A + \beta_A \gamma_B}{\alpha_B \beta_A - \alpha_A \beta_B} \qquad \text{Eq. (29)}$$

Figure 23:
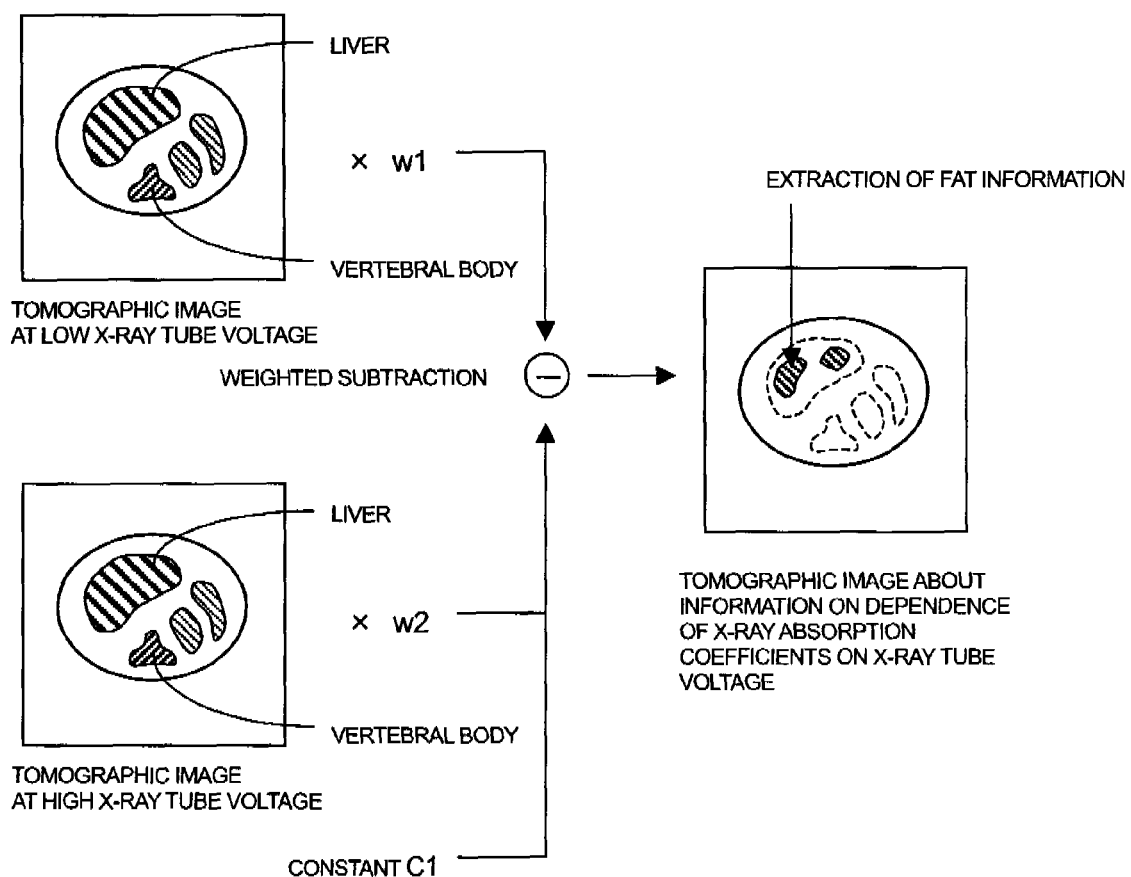
FIG. 23 is a diagram illustrating how to determine tomographic images corresponding to information about the dependence of X-ray absorption coefficients on X-ray tube voltages in an image space.

That is, distribution images indicative of the existence of the materials X and Y are obtained by the process of weighted addition of the tomographic image $CT_A$ at the low X-ray tube voltage and the tomographic image $CT_B$ at the high X-ray tube voltage. A method for determining an existence distribution image of a material X by the process of weighted addition of a tomographic image $CT_A$ at a low X-ray tube voltage and a tomographic image $CT_B$ at a high X-ray tube voltage in an image space is shown in FIG. 23.

X-ray projection data about the materials X and Y can be obtained by the weighted addition process in like manner even in a projection data space. Tomographic images of the materials X and Y can be obtained by image-reconstructing the X-ray projection data about the materials X and Y.

Namely, assuming that X-ray projection data at a low X-ray tube voltage is RA, X-ray projection data at a high X-ray tube voltage is RB, X-ray projection data about the material X is RX, and X-ray projection data about the material Y is RY, the X-ray projection data about the material X and the X-ray projection data about the material Y are determined as expressed in the following Equations (30) and (31):

$$R_X = w1 \cdot R_A + w2 \cdot R_B + c1 \qquad \text{Eq. (30)}$$

$$R_Y = w3 \cdot R_A + w4 \cdot R_B + c2 \qquad \text{Eq. (31)}$$

Tomographic images of the materials X and Y can be obtained by image-reconstructing the X-ray projection data RX about the material X and the X-ray projection data RY about the material Y. Incidentally, the above-described weighted addition process is also called weighted subtraction process because the constants w2 and w4 become negative constants respectively.

Figure 24:
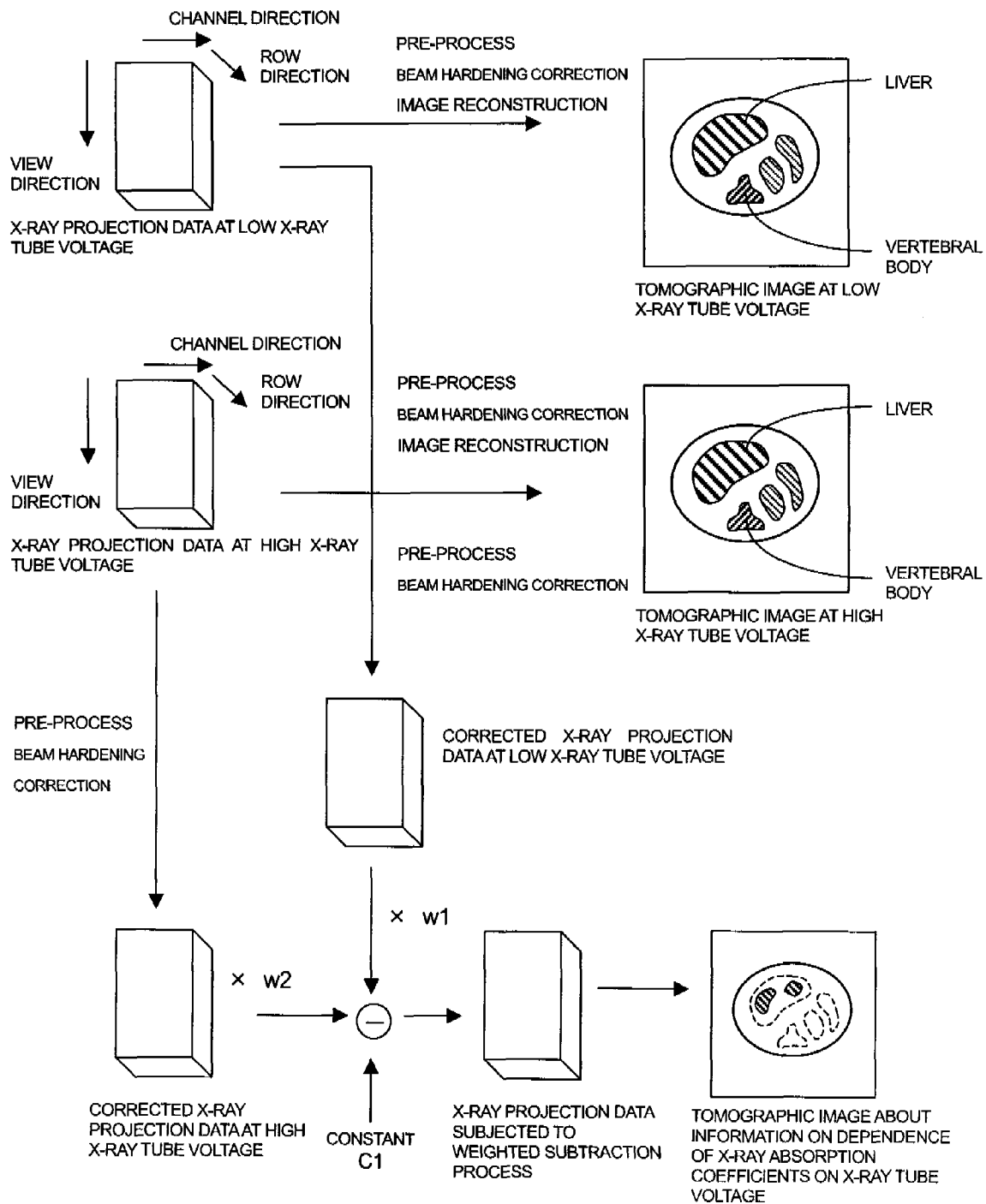
FIG. 24 is a diagram showing how to determine tomographic images corresponding to information about the dependence of X-ray absorption coefficients on X-ray tube voltages in a projection data space.

FIG. 24 shows that X-ray projection data RA at a low X-ray tube voltage and X-ray projection data RB at a high X-ray tube voltage are determined using a weighted addition process of X-ray projection data in a projection data space, and these are image-reconstructed, whereby a tomographic image at the low X-ray tube voltage and a tomographic image at the high X-ray tube voltage are obtained.

As the X-ray projection data used at this time, X-ray projection data subjected to a pre-process and a beam hardening correction is used. In the beam hardening correction in particular, the dependence of an X-ray absorption coefficient of each material other than water on the X-ray tube voltage can be evaluated more properly by setting a water-equivalent X-ray penetration path length at each X-ray tube voltage.

Here, a description will be made of image noise where a weighted addition process of the tomographic image at the low X-ray tube voltage and the tomographic image at the high X-ray tube voltage is performed and a ratio/sum-value difference image with respect to both images is determined.

When an image of difference between a tomographic image at a low X-ray tube voltage in which image noise is n1, a signal level is s1 and an S/N ratio is n1/s1, and a tomographic image at a high X-ray tube voltage in which image noise is n2, a signal level is s2 and an S/N ratio is n2/s2, is determined, an S/N ratio Nsub of the difference image is expressed in the following Equation (32):

$$Nsub = \frac{\sqrt{(n1)^2 + (n2)^2}}{s1 - s2} \quad \text{Eq. (32)}$$

N1 corresponding to the S/N ratio of the tomographic image at the low X-ray tube voltage, and N2 corresponding to the S/N ratio of the tomographic image at the high X-ray tube voltage are respectively expressed in the following Equations (33) and (34):

$$N1 = \frac{n1}{s1} \quad \text{Eq. (33)}$$

$$N2 = \frac{n2}{s2} \quad \text{Eq. (34)}$$

The relation between the following Equations (35) and (36) is found out from these. It is understood that the image noise of the tomographic images for the difference image become larger than the original low X-ray tube voltage and high X-ray tube voltage.

$$N1 < Nsub \quad \text{Eq. (35)}$$

$$N2 < Nsub \quad \text{Eq. (36)}$$

Incidentally, the following Equation (37) below is established by the theorem of the arithmetic and geometric means.

$$\sqrt{2}n1 \leq \sqrt{(n1)^2 + (n2)^2} \quad \text{Eq. (37)}$$

where the equality is established where n1=n2 and where the equality is set up in the case of n1=n2.

Therefore, the S/N ratio Nsub of the difference image is established as expressed in the following Equation (38):

$$\frac{n1}{s1 - s2} \leq Nsub \quad \text{Eq. (38)}$$

where the equality is established where n1=n2 and where the equality is set up in the case of n1=n2.

That is, it is understood that when the image noise n1 of the tomographic image at the low X-ray tube voltage and the image noise n2 of the tomographic image at the high X-ray tube voltage are equal to each other, the image noise Nsub of the difference image becomes the minimum.

Incidentally, the ratio between the image noise n1 of the tomographic image at the low X-ray tube voltage and the image noise n2 of the tomographic image at the high X-ray tube voltage may preferably be about 10% or less or about 5% or less.

Figure 7:
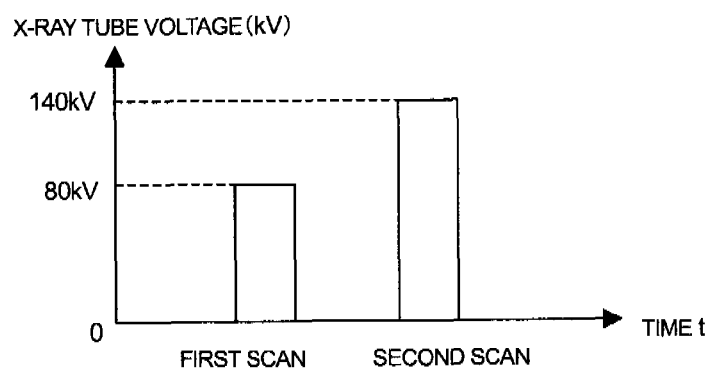
FIG. 7 is a diagram showing a known case in which X-ray tube voltages are switched in scan units.

Incidentally, the scan at the low X-ray tube voltage at Step K6 in FIG. 12, and the scan at the high X-ray tube voltage at Step K7 have heretofore been performed as in the case where, for example, tomographic image photography at a low X-ray tube voltage and tomographic image photography at a high X-ray tube voltage have been performed at first and second scan respectively as shown in FIG. 7.

When, however, spare time is made between the first scan and the second scan, the tomographic image or X-ray projection data at the first scan, and the tomographic image or X-ray projection data at the second scan are shifted in position due to the influence of body motion or the like, so such shifts in position might occur as measurement errors and artifacts upon generation of a distribution image having energy characteristics corresponding to the dependence of X-ray absorption coefficients indicative of distributions of atoms constituting each material on each X-ray tube voltage.

Therefore, there has been a demand for such a scan as to prevent the body motion of the subject.

Figure 8A:
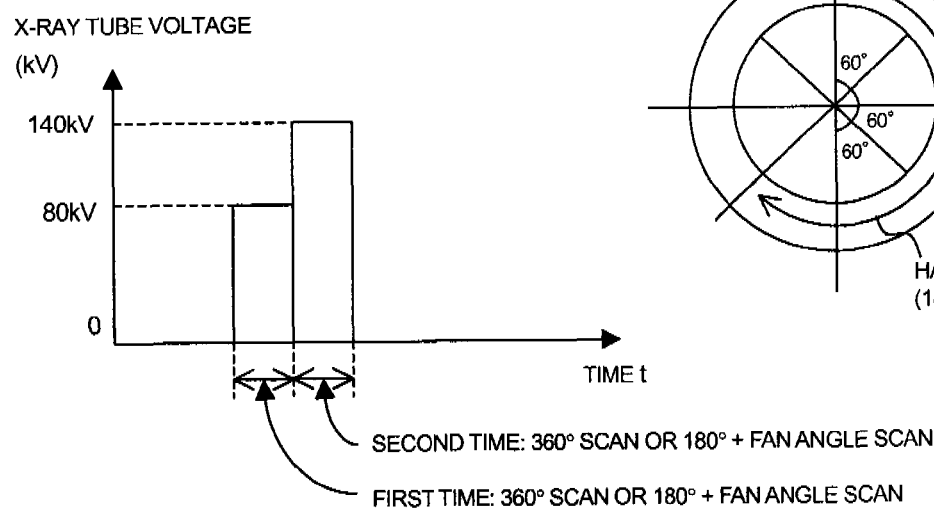
FIGS. 8A and 8B are diagrams illustrating a case in which X-ray tube voltages are switched at sequential scans.
Figure 8B:
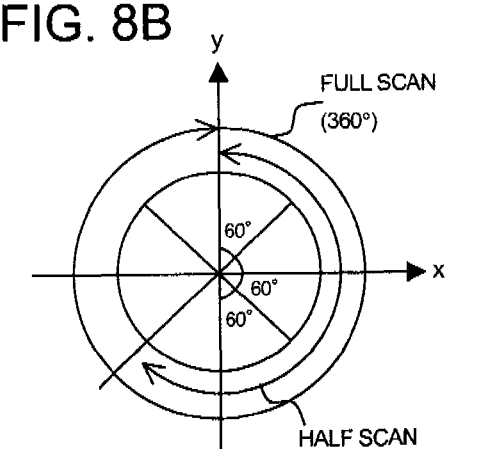

In the present embodiment, a first scan (tomographic image photography at low tube voltage) and a second scan (tomographic image photography at high tube voltage) are performed continuously as shown in FIGS. 8A and 8B. Alternatively, the process of minimizing the body motion of the subject by changing the X-ray tube voltage with slight spare time and performing the scan immediately is performed. Incidentally, although the tomographic image photography at the high X-ray tube voltage of 140 kV is performed after the tomographic image photography at the low X-ray tube voltage of 80 kV has been performed in FIGS. 8A and 8B, the order of the tomographic image photography at the low X-ray tube voltage of 80 kV and the tomographic image tomography image photography at the high X-ray tube voltage of 140 kV may be reversed. Alternatively, the period during which the X rays are off as shown in FIG. 9 to raise the X-ray tube voltage as described above, may be interposed.

Figure 9:
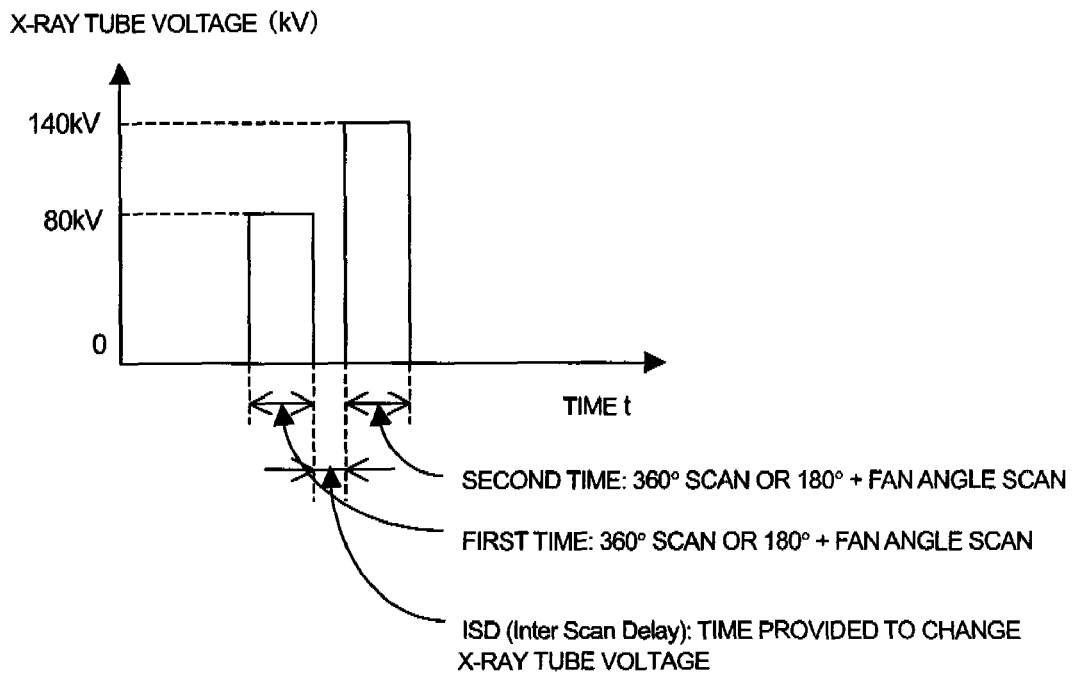
FIG. 9 is a diagram depicting a case in which X-ray tube voltages are switched at sequential scans.
Figure 10:
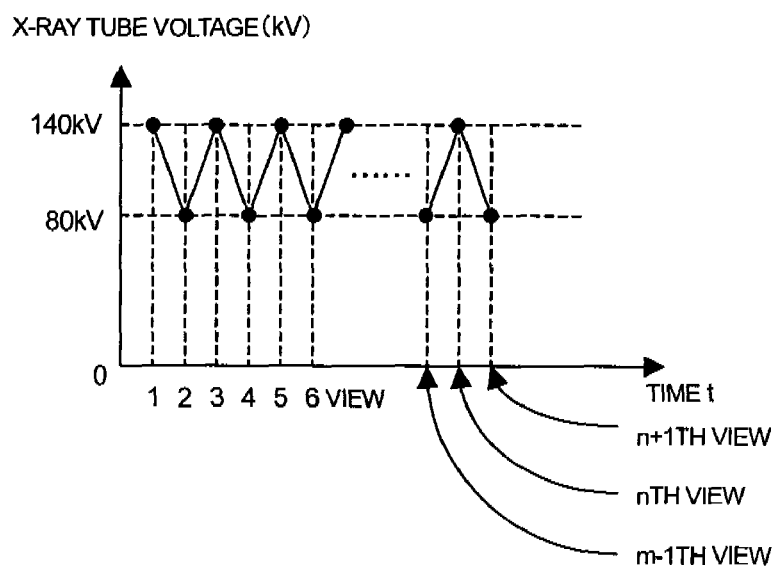
FIG. 10 is a diagram showing a case in which X-ray tube voltages are switched for every view.

When it is desired to cause an X-ray data acquisition start view angle for X-ray projection data at a low X-ray tube voltage and an X-ray data acquisition start view angle for X-ray projection data at a high X-ray tube voltage to coincide with each other in order to perform processing on the X-ray projection data, the time of ISD (Inter Scan Delay) corresponding to an X-ray off time between a first scan and a second scan shown in FIG. 9 is adjusted so that the data acquisition start view angle at the first scan and the data acquisition start view angle at the second scan can be matched.

Further, as a scan method for more reducing the body motion of the subject, there is known, for example, a method for changing X-ray tube voltages every view as shown in FIG.

Figure 11:
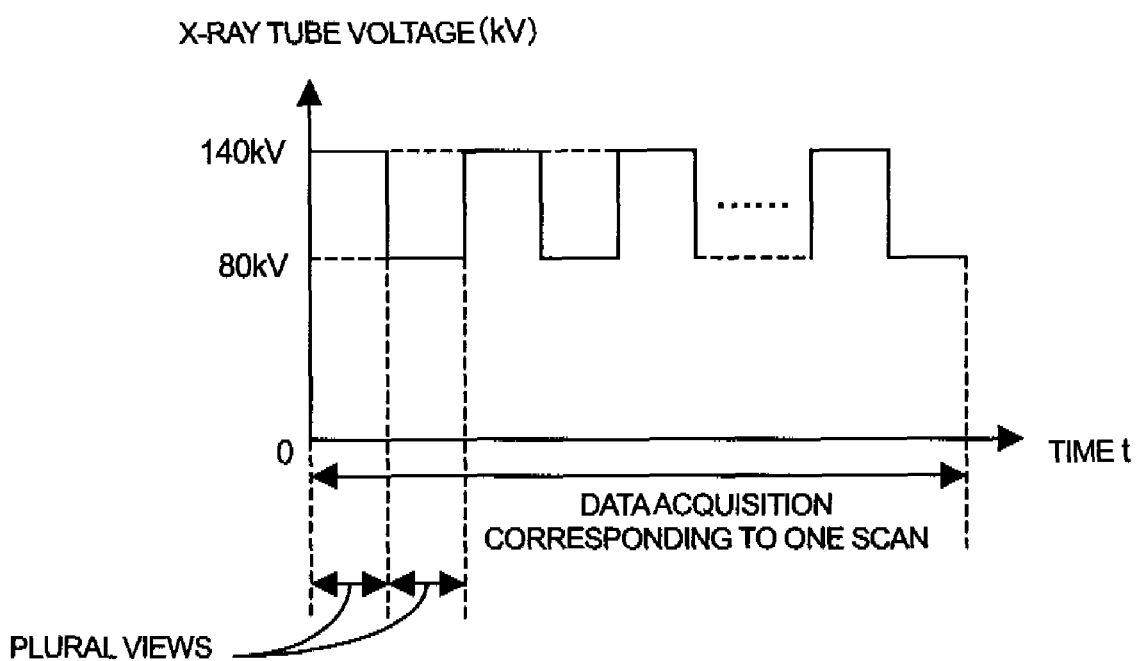
FIG. 11 is a diagram illustrating a case in which X-ray tube voltages are switched for every data acquisition segment.

10 as X-ray data acquisition at a high X-ray tube voltage of 140 kV with respect to odd views or X-ray data acquisition at a low X-ray tube voltage of 80 kV with respect to even views. Alternatively, X-ray data acquisition at a high X-ray tube voltage of 140 kV and X-ray data acquisition at a low X-ray tube voltage of 80 kV may be alternately carried out every units of plural unified views as shown in FIG. 11.

In either case, the X-ray projection data at the high X-ray tube voltage 140 kV and the low X-ray tube voltage 80 kV may finally be acquired by 360° or 180°+fan angle. The order of the high X-ray tube voltage 140 kV and the low X-ray tube voltage 80 kV may be reversed. The X-ray tube voltage value may be a value other than 140 kV and 80 kV.

The present embodiment shows an embodiment in which an X-ray penetration path length corresponding to a profile distribution of a subject is determined from a scout image obtained by a helical scout scan, and X-ray tube currents at a low X-ray tube voltage (80 kV, for example) and a high X-ray tube voltage (140 kV, for example) are determined from geometrical characteristic amounts of profiles of the subject.

When the scout image is determined by the helical scout scan, tomographic images continuous in two directions are first image-reconstructed and thereafter a reprojection process is performed in a 0° or 90° direction or another angular direction to determine the corresponding scout image.

The reprojection process can be performed in any direction including an x-axis direction and a y-axis direction as a reprojection direction in this case. In ether case, the reprojection process becomes a parallel beam reprojection process, and the scout image based on the parallel beam reprojection can be image-reconstructed in this way. That is, the parallel-beam reprojection scout image can be brought into imaging on a proper scale at all times even though it is close to or distant from an X-ray focal point. Therefore, the proper geometrical characteristic amounts of the subject are obtained without depending on the distance between the X-ray focal point and the subject even though the subject is at any location of a field of view for photography, and the optimum imaging condition at each z-direction coordinate position at which uniform image quality is obtained in the z direction, can be set.

A tomographic image at each z-direction coordinate position is obtained upon the helical scout scan in particular. Of the tomographic image, a portion that cannot be corrected sufficiently upon the normal beam hardening correction, i.e., a region of part indicative of such a characteristic as different from water in X-ray absorption coefficient, e.g., a bone portion or region is extracted to determine correction data of a penetration path. The X-ray penetration path length determined by the pre-process and beam hardening correction can be obtained with more satisfactory accuracy.

FIG. 25 shows a flow chart used where imaging conditions for two types of X-ray tube voltages are decided using the scout image obtained at the helical scout scan according to the present embodiment.

At Step K11, the subject is placed on the cradle 12 of the photographing table 10 and its alignment is performed.

At Step K12, the helical scout scan is performed.

At Step K13, image reconstruction at the helical scout scan is carried out.

At Step K14, each continuous tomographic image is set as a three-dimensional image and a bone's portion or region is extracted from the three-dimensional image.

At Step K15, a penetration path for the bone and a penetration path for the overall subject are determined.

At Step K16, a penetration path for a low X-ray tube voltage and a penetration path for a high X-ray tube voltage are determined.

At Step K17, respective X-ray tube current values for an imaging condition at the low X-ray tube voltage and an imaging condition at the high X-ray tube voltage are determined to set the corresponding imaging conditions.

At Step K18, a scan at the low X-ray tube voltage is performed.

At Step K19, a scan at the high X-ray tube voltage is performed.

At Step K20, a material discrimination image dependent on the X-ray tube is image-reconstructed.

At Step K21, the material discrimination image is displayed.

At Step K15 referred to above, each tomographic image continuous in the z direction is determined once by the helical scout scan based on the ultra-low exposure scan at Step K15, and thereafter a reprojection process is performed in the 0° or 90° direction or another angular direction to determine the corresponding scout image. Therefore, tomographic image information is known upon the setting of the imaging conditions.

At this time, a region in which each material likely to indicate a characteristic having a tendency different in X-ray absorption coefficient from water as in the bone and the contrast agent exists is detected. A penetration path length of an X-ray beam that passes through the region is determined, and a correction can be performed on the conversion to a water-equivalent X-ray path length that could not be corrected by the beam hardening correction.

At Step K16 referred to above, a penetration path length at a low X-ray tube voltage and a penetration path length at a high X-ray tube voltage are determined by correcting characteristics different from water in bone's X-ray absorption coefficient that differs depending on each X-ray tube voltage.

FIG. 26 shows a flow of Step K15 for determining profile distributions for regions or areas of a bone and a contrast agent and determining correction data about each water-equivalent path length.

At Step B1, a tomographic image at a helical scout scan is inputted.

At Step B2, the range of a CT value (greater than or equal to a CT value 200, for example) is set, and a binarization process is performed on the region of the bone or contrast agent.

At Step B3, a CT-value standard deviation of an adjacent region at each pixel in the extracted binarized region is determined.

At Step B4, the region of the bone and the region of the contract agent are separated from each other.

At Step B5, profile distributions in respective view directions for the region of the bone and the region of the contrast agent are determined.

At Step B6, correction data for the regions of the bone and contrast agent in the respective view directions are determined.

At Step B7, the water-equivalent path lengths in the respective view directions are corrected.

According to the X-ray CT apparatus 100 of the present invention as described above, an advantage is brought about in that a reduction in exposure and an improvement in image quality are realized upon imaging or photography for obtaining each tomographic image indicative of X-ray tube voltage dependent information.

The present invention can obtain a similar advantage by using similar imaging conditions for a plurality of tomographic images continuous in the z direction (body-axis direction of subject).

Incidentally, although the above embodiment has used the X-ray tube currents as the parameters for controlling the optimum imaging conditions, the imaging conditions may be controlled by parameters such as a helical pitch at a helical scan, an image filter, a reconstruction function, a z filter, a slice thickness, a scan time interval, etc. in addition to the X-ray tube currents to set the optimum imaging conditions under which uniform image quality is obtained in the z direction.

Incidentally, although the present embodiment has described the two types of X-ray tube voltages 80 kV and 140 kV under the two types of imaging conditions, X-ray tube voltages different from 80 kV and 140 kV may be combined. Further, a similar advantage can be brought about even in the case of three or more types of imaging conditions and X-ray tube voltages.

Incidentally, the image reconstructing method according to the present invention may be a three-dimensional image reconstructing method based on a conventional known Feldkamp method. Further, another three-dimensional image reconstructing method may be adopted. Alternatively, two-dimensional image reconstruction may be used.

The present invention is capable of bringing about an advantage similarly even in the case of a conventional scan (axial scan), a cine scan and a variable-pitch helical scan.

The present invention can bring about a similar advantage even in the case of a so-called tilt scan in which the scan gantry 20 is tiled.

The present invention can bring about a similar advantage even when synchronization with a biological signal, particularly, a cardiac signal is taken.

In the present invention, a similar advantage can be brought about even in the case of an X-ray CT apparatus having a two-dimensional X-ray area detector of matrix structure, which is typified by the multi-row X-ray detector or the flat panel X-ray detector, or a one-row X-ray detector.

In the present embodiment, the row-direction (z-direction) filters different in coefficient for every row are convolved or overlaid, thereby adjusting variations in image quality and realizing a uniform slice thickness, artifacts and the image quality of noise at each row. Although various z-direction filter coefficients are considered therefore, any can bring about a similar advantage.

Although the present embodiment has been described on the basis of the medical X-ray CT apparatus, it can be made available to an X-ray CT-PET apparatus utilized in combination with an industrial X-ray CT apparatus or another apparatus, an X-ray CT-SPECT apparatus utilized in combination therewith, etc.

The invention claimed is:

1. An X-ray computed tomography (CT) apparatus comprising:
    an X-ray generator and an X-ray detector arranged opposite to said X-ray generator, said X-ray generator and said X-ray detector configured to rotate about a center of rotation, said X-ray detector further configured to detect X-rays transmitted by said X-ray generator through a subject;
    a condition setting device configured to set a plurality of X-ray tube voltages for use in acquiring X-ray projection data;
    an X-ray data acquisition device configured to acquire a respective X-ray projection data set for each of the plurality of X-ray tube voltages;
    an image reconstruction device configured to image-reconstruct X-ray projection data sets acquired by said X-ray data acquisition device to form a plurality of tomographic images; and
    an image display configured to display the plurality of tomographic images,
    wherein said condition setting device is further configured to calculate a respective value of an imaging condition for each of the plurality of X-ray tube voltages such that respective image noise values associated with each of the plurality of X-ray tube voltages are substantially identical to one another, and to set the imaging condition to the calculated value for acquiring the X-ray projection data using the plurality of X-ray tube voltages.

2. The X-ray CT apparatus according to claim 1, wherein the image condition is an X-ray tube current.

3. The X-ray CT apparatus according to claim 2, wherein the X-ray tube current is calculated based on geometrical characteristic amounts of the subject determined from a scout image.

4. The X-ray CT apparatus according to claim 3, wherein the scout image is obtained based on different X-ray tube voltages used to obtain the plurality of tomographic images, and the X-ray tube current is calculated by correcting the subject's geometrical characteristic amounts of the subject based on the scout image to amounts equivalent to the X-ray tube voltages used to obtain the plurality of tomographic images.

5. The X-ray CT apparatus according to claim 4, wherein the correction is based on a difference between X-ray penetration path lengths at respective X-ray tube voltages, which have been determined from the scout image.

6. The X-ray CT apparatus according to claim 5, wherein the correction is based on a difference between respective X-ray tube voltages, which has been determined using penetration path lengths set for each of the plurality of X-ray tube voltages in a partial region comprised of a predetermined material from a tomographic image obtained using a helical scout scan.

7. The X-ray CT apparatus according to claim 6, wherein the partial region comprised of the predetermined material of the tomographic image obtained using the helical scout scan is of a region defined by a range of a predetermined CT value.

8. The X-ray CT apparatus according to claim 3, wherein said condition setting device is configured to set an index of desired image noise and to calculate each X-ray tube current for use in acquiring the X-ray projection data using each of the plurality of X-ray tube voltages such that the image noise is substantially identical to the index of desired image noise for each of the plurality of X-ray tube voltages.

9. The X-ray CT apparatus according to claim 1, wherein said image reconstruction device is configured to extract X-ray tube voltage dependent information using the X-ray projection data obtained using photography of the plurality of X-ray tube voltages and to bring the same into imaging.

10. The X-ray CT apparatus according to claim 9, wherein said image reconstruction device is configured to extract the X-ray tube voltage dependent information by the photography of the plurality of X-ray tube voltages and to bring the same into imaging within an image space.

11. The X-ray CT apparatus according to claim 9, wherein said image reconstruction device is configured to extract the X-ray tube voltage dependent information by the photography of the plurality of X-ray tube voltages and to bring the same into imaging within an X-ray projection data space.

12. The X-ray CT apparatus according to claim 10, wherein said image reconstruction device is configured to extract the X-ray tube voltage dependent information and to bring the same into imaging using a weighted subtraction process.

13. The X-ray CT apparatus according to claim 9, wherein the X-ray tube voltage dependent information is information dependent on each material within the subject.

14. An X-ray computed tomography (CT) apparatus comprising:
    an X-ray generator and an X-ray detector arranged opposite to said X-ray generator, said X-ray generator and said X-ray detector configured to rotate about a center of rotation, said X-ray detector further configured to detect X-rays transmitted by said X-ray generator through a subject;
    a condition setting device configured to set a first X-ray tube voltage and a second X-ray tube voltage that is different than the first X-ray tube voltage for use in acquiring X-ray projection data;

an X-ray data acquisition device configured to acquire a first X-ray projection data set corresponding to the first X-ray tube voltage and a second X-ray projection data set corresponding to the second X-ray tube voltage;

an image reconstruction device configured to image-reconstruct X-ray projection data acquired from said X-ray data acquisition device to form a tomographic image; and an image display configured to display the image-reconstructed tomographic image, wherein said condition setting device is further configured to calculate a first X-ray tube current using the first X-ray tube voltage and a second X-ray tube current using the second X-ray tube voltage.

15. The X-ray CT apparatus according to claim 14, wherein the first X-ray tube current and the second X-ray tube current are calculated such that respective image noise associated with each of the first X-ray tube voltage and the second X-ray tube voltage is substantially identical to one another.

16. The X-ray CT apparatus according to claim 14, wherein the first X-ray voltage is 80 kV.

17. The X-ray CT apparatus according to claim 14, wherein the second X-ray voltage is 140 kV.

18. The X-ray CT apparatus according to claim 14, wherein said image reconstruction device is configured to produce an image based on X-ray tube voltage dependent information using the X-ray projection data corresponding to the first X-ray tube voltage and the second X-ray tube voltage.

19. The X-ray CT apparatus according to claim 18, wherein said image reconstruction device is configured to produce an image based on X-ray tube voltage dependent information by weighted subtraction of first X-ray projection data corresponding to the first X-ray tube voltage and second X-ray projection data corresponding to the second X-ray tube voltage.

20. The X-ray CT apparatus according to claim 18, wherein said image reconstruction device is configured to produce an image based on X-ray tube voltage dependent information by weighted subtraction of a first tomographic image reconstructed using first X-ray projection data corresponding to the first X-ray tube voltage and a second tomographic image reconstructed using second X-ray projection data corresponding to the second X-ray tube voltage.

* * * * *